US006214547B1

(12) United States Patent
Kjeldsen et al.

(10) Patent No.: US 6,214,547 B1
(45) Date of Patent: Apr. 10, 2001

(54) SYNTHETIC LEADER PEPTIDE SEQUENCES

(75) Inventors: Thomas Børglum Kjeldsen, Virum; Svend Havelund, Bagsværd; Annette Frost Petterson, Farum; Per Balschmidt, Espergærde, all of (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/012,669

(22) Filed: Jan. 23, 1998

Related U.S. Application Data

(63) Continuation of application No. PCT/DK98/00026, filed on Jan. 22, 1998.

(30) Foreign Application Priority Data

Jan. 24, 1997 (DK) .................................................. 0092/97

(51) Int. Cl.[7] ............................ C12Q 1/68; C12N 15/63; C12N 1/14; C12P 21/00; C07H 21/04

(52) U.S. Cl. ........................... 435/6; 435/69.1; 435/69.9; 435/91.4; 435/255.1; 435/320.1; 536/23.1; 536/23.74; 536/24.1; 536/24.2

(58) Field of Search ............................. 435/6, 69.1, 69.9, 435/91.4, 320.1, 255.1; 536/23.1, 23.74, 24.1, 24.2

(56) References Cited

U.S. PATENT DOCUMENTS 5,514,585 * 5/1996 Bjorn et al. .................... 435/254.11
5,861,267 * 1/1999 Su ......................................... 435/23

FOREIGN PATENT DOCUMENTS

WO 95/34666 12/1995 (EP) .
WO95/02059 * 1/1995 (WO) ............................... 435/255.1

OTHER PUBLICATIONS

Sztul et al. Import of the malated dehydrogenase precursor by mitochondria. J. Biol. Chem. Vo. 263:(24):12085–12091, Aug. 1988.*

Abstract; Pap. Am. Chem. Soc., vol. 196 Meet, MBTD 37, H.M. Sassenfeld et al. : "A general strategy for the expression and purification of lymphokines". Sep. 1996.

Clements et al., "Secretion of Human Epidermal Growth Factor from *Saccharomyces Cerevisiae* Using Synthetic Leader Sequences", Gene 106, (1991) pp. 267–271.

Laroche et al., High–Level Secretion and Very Efficient Isotopic Labeling of Tick Anticoagulant Peptide (TAP) Expressed in the Methylotrophic Yeast, *Pichia Pastoris,* Biotechnology vol. 12, Nov. 1994, pp. 1119–1124.

* cited by examiner

*Primary Examiner*—Robert A. Schwartzman
*Assistant Examiner*—William Sandals
(74) *Attorney, Agent, or Firm*—Steve T. Zelson; Valeta Gregg

(57) ABSTRACT

The present invention relates to synthetic leader peptide sequences for secreting polypeptides in yeast.

34 Claims, 7 Drawing Sheets

```
                                                      EcoRI
                                                      ~~~~~~~
901   TTCTTGCTTA AATCTATAAC TACAAAAAAC ACATACAGGA ATTCCATTCA
      AAGAACGAAT TTAGATATTG ATGTTTTTTG TGTATGTCCT TAAGGTAAGT

951   AGAATAGTTC AAACAAGAAG ATTACAAACT ATCAATTTCA TACACAATAT
      TCTTATCAAG TTTGTTCTTC TAATGTTTGA TAGTTAAAGT ATGTGTTATA

  +1                   M  K   L  K  T  V   R  S  A   V  L  S
                                           Bg1II
                                           ~~~~~~
1001  AAACGATTAA AAGAATGAAA CTGAAAAACTG TAAGATCTGC GGTCCTTTCG
      TTTGCTAATT TTCTTACTTT GACTTTTGAC ATTCTAGACG CCAGGAAAGC

  +1  S  L  F  A   S  Q  V   L  G  Q   P  I  D  D   T  E  S
                            StyI
                            ~~~~~~
1051  TCACTCTTTG CATCTCAGGT CCTTGGCCAA CCAATTGACG ACACTGAATC
      AGTGAGAAAC GTAGAGTCCA GGAACCGGTT GGTTAACTGC TGTGACTTAG

  +1   Q  T  T   S  V  N  L   M  A  D   D  T  E   S  A  F
1101  TCAAACTACT TCTGTCAACT TGATGGCTGA CGACACTGAA TCTGCTTTCG
      AGTTTGATGA AGACAGTTGA ACTACCGACT GCTGTGACTT AGACGAAAGC

  +1 A  T  Q  T   N  S  G   G  L  D  V   V  G  L   I  S  M
                                                         StyI
                                                         ~~~~~
                                                         NcoI
                                                         ~~~~~
```

FIG 2A

```
1151  CTACTCAAAC TAACTCTGGT GGTTTGGATC TTGTTGGTTT GATCTCCATG
      GATGAGTTTG ATTGAGACCA CCAAACCTAC AACAACCAAA CTAGAGGTAC

  +1  A  K  R  E   E  G  E   P  K  F   V  N  Q  H   L  C  G
      StyI
      ~
      NcoI
      ~
1201  GCTAAGAGAG AAGAAGGTGA ACCAAAGTTC GTTAACCAAC ACTTGTGCGG
      CGATTCTCTC TTCTTCCACT TGGTTTCAAG CAATTGGTTG TGAACACGCC

  +1   S  H  L   V  E  A  L   Y  L  V   C  G  E   R  G  F
                    HindIII
                    ~~~~~~
1251  TTCCCACTTG GTTGAAGCTT TGTACTTGGT TTGCGGTGAA AGAGGTTTCT
      AAGGGTGAAC CAACTTCGAA ACATGAACCA AACGCCACTT TCTCCAAAGA

  +1  F  Y  T  P   K  A  A   K  G  I  V   E  Q  C   C  T  S
              Bsu36I
              ~~~~~~~~~
1301  TCTACACTCC TAAGGCTGCT AAGGGTATTG TCGAACAATG CTGTACCTCC
      AGATGTGAGG ATTCCGACGA TTCCCATAAC AGCTTGTTAC GACATGGAGG

  +1   I  C  S  L   Y  Q  L   E  N  Y   C  N  *
1351  ATCTGCTCCT TGTACCAATT GGAAAACTAC TGCAACTAGA CGCAGCCCGC
      TAGACGAGGA ACATGGTTAA CCTTTTGATG ACGTTGATCT GCGTCGGGCG

         ~XbaI
         ~~~~~~
1401  AGGCTCTAGA AACTAAGATT AATATAATTA TATAAAAATA TTATCTTCTT
      TCCGAGATCT TTGATTCTAA TTATATTAAT ATATTTTTAT AATAGAAGAA
```

FIG 2B

```
                                                        EcoRI
901   TTCTTGCTTA AATCTATAAC TACAAAAAAC ACATACAGGA ATTCCATTCA
      AAGAACGAAT TTAGATATTG ATGTTTTTTG TGTATGTCCT TAAGGTAAGT

951   AGAATAGTTC AAACAAGAAG ATTACAAACT ATCAATTTCA TACACAATAT
      TCTTATCAAG TTTGTTCTTC TAATGTTTGA TAGTTAAAGT ATGTGTTATA

 +1                       M  K   L  K  T  V   R  S  A   V  L  S
                                               BglII
1001  AAACGATTAA AAGAATGAAA CTGAAAACTG TAAGATCTGC GGTCCTTTCG
      TTTGCTAATT TTCTTACTTT GACTTTTGAC ATTCTAGACG CCAGGAAAGC

 +1   S  L  F  A   S  Q  V   L  G  Q   P  I  D  D   T  E  S
                             StyI
1051  TCACTCTTTG CATCTCAGGT CCTTGGCCAA CCAATTGACG ACACTGAATC
      AGTGAGAAAC GTAGAGTCCA GGAACCGGTT GGTTAACTGC TGTGACTTAG

 +1    Q  T  T   S  V  N  L   M  A  D   D  T  E   S  A  F
1101  TCAAACTACT TCTGTCAACT TGATGGCTGA CGACACTGAA TCTGCTTTCG
      AGTTTGATGA AGACAGTTGA ACTACCGACT GCTGTGACTT AGACGAAAGC

 +1   A  T  Q  T   N  S  G   G  L  D  V   V  G  L   P  G  A
1151  CTACTCAAAC TAACTCTGGT GGTTTGGATG TTGTTGGTTT GCCAGGTGCT
      GATGAGTTTG ATTGAGACCA CCAAACCTAC AACAACCAAA CGGTCCACGA

 +1   K  R  F  V   N  Q  H   L  C  G   S  H  L  V   E  A  L
                                                    HindIII
1201  AAGAGATTCG TTAACCAACA CTTGTGCGGT TCCCACTTGG TTGAAGCTTT
      TTCTCTAAGC AATTGGTTGT GAACACGCCA AGGGTGAACC AACTTCGAAA

 +1    Y  L  V   C  G  E  R   G  F  F   Y  T  P   K  A  A
                                              Bsu36I
1251  GTACTTGGTT TGCGGTGAAA GAGGTTTCTT CTACACTCCT AAGGCTGCTA
      CATGAACCAA ACGCCACTTT CTCCAAAGAA GATGTGAGGA TTCCGACGAT

 +1   K  G  I  V   E  Q  C   C  T  S  I   C  S  L   Y  Q  L
1301  AGGGTATTGT CGAACAATGC TGTACCTCCA TCTGCTCCTT GTACCAATTG
      TCCCATAACA GCTTGTTACG ACATGGAGGT AGACGAGGAA CATGGTTAAC

 +1    E  N  Y  C   N  *
                                         XbaI
1351  GAAAACTACT GCAACTAGAC GCAGCCCGCA GGCTCTAGAA ACTAAGATTA
      CTTTTGATGA CGTTGATCTG CGTCGGGCGT CCGAGATCTT TGATTCTAAT
```

FIG 3

SYNTHETIC LEADER PEPTIDE SEQUENCES

CROSS-REFERENCE TO RELATED APPLICATIONS

This application is a continuation of PCT/DK98/00026 filed Jan. 22, 1998, the contents of which are fully incorporated herein by reference. The contents of Danish application 0092/97 filed Jan. 24, 1997 are fully incorporated herein by reference.

FIELD OF INVENTION

The present invention relates to novel synthetic leader peptide sequences for secreting polypeptides in yeast.

BACKGROUND OF THE INVENTION

Yeast organisms produce a number of proteins which are synthesized intracellularly, but which have a function outside the cell. Such extracellular proteins are referred to as secreted proteins. These secreted proteins are expressed initially inside the cell in a precursor or a pre-protein form containing a pre-peptide sequence ensuring effective direction of the expressed product (into the secretory pathway of the cell) across the membrane of the endoplasmic reticulum (ER). The pre-sequence, normally named a signal peptide, is generally cleaved off from the desired product during translocation. Once entered in the secretory pathway, the protein is transported to the Golgi apparatus. From the Golgi the protein can follow different routes that lead to compartments such as the cell vacuole or the cell membrane, or it can be routed out of the cell to be secreted to the external medium (Pfeffer, S. R. and Rothman, J. E. *Ann.Rev.Biochem.* 56 (1987) 829–852).

Several approaches have been suggested for the expression and secretion in yeast of proteins heterologous to yeast. European published patent application No. 88 632 describes a process by which proteins heterologous to yeast are expressed, processed and secreted by transforming a yeast organism with an expression vehicle harbouring DNA encoding the desired protein and a signal peptide, preparing a culture of the transformed organism, growing the culture and recovering the protein from the culture medium. The signal peptide may be the signal peptide of the desired protein itself, a heterologous signal peptide or a hybrid of native and heterologous signal peptides.

A problem encountered with the use of signal peptides heterologous to yeast might be that the heterologous signal peptide does not ensure efficient translocation and/or cleavage ot the precursor polypeptide after the signal peptide.

The *Saccharomyces cerevisiae* MFα1 (α-factor) is synthesized as a pre-pro form of 165 amino acids comprising signal- or pre-peptide of 19 amino acids followed by a "leader" or pro-peptide of 64 amino acids, encompassing three N-linked glycosylation sites followed by (LysArg$((Asp/Glu)Ala)_{2-3}$α-factor$)_4$ (Kurjan, J. and Herskowitz, I. *Cell* 30 (1982) 933–943). The signal-leader part of the pre-pro MFα1 has been widely employed to obtain synthesis and secretion of heterologous proteins in *S. cerevisiae.*

Use of signal/leader peptides homologous to yeast is known from i. a. U.S. Pat. No. 4,546,082, European published patent applications Nos. 116 201, 123 294, 123 544, 163 529 and 123 289 and DK patent application No. 3614/83.

In EP 123 289 utilization of the *S. cerevisiae* α-factor precursor is described whereas WO 84/01153 indicates utilization of the *S. cerevisiae* invertase signal peptide and DK 3614/83 utilization of the *S. cerevisiae* PH05 signal peptide for secretion of foreign proteins.

U.S. Pat. No. 4,546,082, EP 16 201, 123 294, 123 544 and 163 529 describe processes by which the α-factor signal-leader from *S. cerevisiae* (MFa1 or MFα2) is utilized in the secretion process of expressed heterologous proteins in yeast. By fusing a DNA sequence encoding the *S. cerevisiae* MFα1 signal/leader sequence at the 5' end of the gene for the desired protein secretion and processing of the desired protein was demonstrated.

EP 206 783 discloses a system for the secretion of polypeptides from *S. cerevisiae* using an α-factor leader sequence which has been truncated to eliminate the four α-factor units present on the native leader sequence so as to leave the leader peptide itself fused to a heterologous polypeptide via the α-factor processing site LysArgGluAlaGluAla (SEQ ID NO:51). This construction is indicated to lead to an efficient processing of smaller peptides (less than 50 amino acids). For the secretion and processing of larger polypeptides, the native α-factor leader sequence has been truncated to leave one or two of the α-factor units between the leader peptide and the polypeptide.

A number of secreted proteins are routed so as to be exposed to a proteolytic processing system which can cleave the peptide bond at the carboxy end of two consecutive basic amino acids. This enzymatic activity is in *S. cerevisiae* encoded by the KEX 2 gene (Julius, D. A. et al., *Cell* 37 (1984b) 1075). Processing of the product by the KEX 2 protease is needed for the secretion of active *S. cerevisiae* mating factor α1 (MFα1 or α-factor) whereas KEX 2 is not involved in the secretion of active *S. cerevisiae* mating factor a.

Secretion and correct processing of a polypeptide intended to be secreted is obtained in some cases when culturing a yeast organism which is transformed with a vector constructed as indicated in the references given above. In many cases, however, the level of secretion is very low or there is no secretion, or the proteolytic processing may be incorrect or incomplete resulting in secretion of a considerable amount of leader bound product polypeptide. Prosequences, and especially N-terminally located prosequences, or leader sequences expressed in eucaryotic cells, such as yeast cells, are extensively glycosylated, cf. Fiedler and Simons, Cell, 81, p 309–312; and Moir, D. T., Yeast mutants with increased secretion efficiency, in Yeast Genetic Engineering, Barr, P. J., Brake, A. J., and Valenzuela, P. eds., wherein a general review of glycosylation and secretion of proteins is presented. It is generally recognised that glycosylation, which may be either N-linked, O-linked, or both, is important for efficient transport through the secretory pathway, cf. Caplan et al., Journal of Bacteriology, Vol. 173, No. 2, p. 627–635; and Jars et al., The Journal of Biological Chemistry, Vol. 270, No. 42, p 24810–24817. Moreover, due to the extensive glycosylation the purification of secreted propeptides is difficult and differs considerably from the processing steps that are typically employed for the purification of the mature secreted polypeptide. Clements et al., Gene, 106 (1991) 267–272, have shown that using a eucaryotic consensus signal sequence and two 19-aa pro-sequences comprising fractions of the α-Factor leader and identical except for the presence or absence of a potential Asn linked (N-linked) glycosylation site for secretion of hEGF from yeast had no effect on secretion, and the level of secretion was comparable to the level obtained when using the α-Factor prepro-sequence (about 3 μg/ml).

Expression of heterologous proteins as fusion proteins is a well known concept and has been utilized in various contexts in different organisms. Secretory expression of a heterologous protein in yeast is often performed as a fusion protein with a secretion prepro-leader to confer secretion competence. Prepro-leaders tend to be hyperglycosylated or extensively O-linked glycosylated in the *S. cerecisiae* secretory pathway. Purification of hyperglycosylated fusion protein is laborious due to its heterogeneous nature. Efficient prepro-leaders lacking hyperglycosylation, with no or limited O-linked glycosylation and replacement of the dibasic Kex2 endoprotease site with a more convenient enzymatic processing site, provide an alternative to conventional yeast expression by purification of the fusion protein and subsequently in vitro maturation with a suitable enzyme as exemplified herein for the insulin precursor. In vitro maturation of a purified fusion protein is more flexible since dependency on the Kex2 endoprotease is eliminated and any proteolytic enzyme can be used for maturation provided that the heterologous protein does not have any internal processing sites. Purification of the fusion protein from the culture supernatant followed by in vitro maturation will avoid N-terminal processing of the heterologous protein by dipeptidyl aminopeptidase. Secretion of a fusion protein rather than the heterologous protein has the advantage that the propeptide may increase stability and solubility until purification and maturation. Secretory expression in yeast of heterologous proteins with internal dibasic sites may lead to Kex2 endoprotease processing and a decrease in fermentation yield. This can be avoided by utilizing a secretion prepro-leader lacking N-linked glycosylation to confer secretion competence, introduction of a suitable enzyme processing site between the prepro-leader and the heterologous protein, expression in a Kex2 endoprotease negative *S. cerevisiae* strain followed by purification and in vitro maturation.

It is an object of the present invention to provide novel synthetic leader peptides or pro-sequences which ensure a higher yield and a more efficient recovery and/or processing of polypeptides, preferably secreted polypeptides, including leader bound polypeptides, and polypeptides being fused N-terminally to peptide sequences including leader sequences and/or spacer sequences each of which optionally being separated from the other constituent sequences by a processing site, expressed in a eucaryotic host cell organism, preferably a fungal cell, such as a yeast cell or a filamentous fungus cell.

SUMMARY OF THE INVENTION

A novel type of synthetic leader peptide has been found which allows secretion in high yield and/or improved recovery of a polypeptide produced in yeast.

Accordingly, the present invention relates to a DNA construct encoding a polypeptide and having the structure SP-LP-(PS)-(S)-(PS)-*gene*, wherein SP is a DNA sequence (presequence) encoding a signal peptide, LP is a DNA sequence encoding a synthetic leader peptide (propeptide) wherein N-linked glycosylation is lacking, PS is a DNA sequence encoding a protease processing site which is optional, S is a DNA sequence encoding a spacer peptide, and *gene* is a DNA sequence encoding a polypeptide. The structure SP-LP-(PS)-(S)-(PS)-*gene* comprises the following structures, SP-LP-PS-S-PS-*gene*, SP-LP-PS-*gene*, SP-LP-PS-S-*gene*, SP-LP-S-*gene*, SP-LP-S-PS-*gene*, and SP-LP-*gene*; in structures containing more than one PS these may be the same or different.

Preferably, PS is a DNA sequence encoding a yeast protease processing site, such as an endopeptidase processing site, and LS is preferably a DNA sequence encoding a synthetic leader peptide or prepro-leader of SEQ ID NOS:38 and 39.

Xaa Pro Ile Asp Asp Thr Glu Ser Gln Thr Thr Ser Val Asn Leu Met Ala Asp Asp Thr Glu Ser Xaa Phe Ala Thr Xaa Thr Xaa Xaa Xaa Xaa Xaa Leu Asp Val Val Xaa Leu Ile Ser Met Ala Xaa Xaa (SEQ ID NO:38) and Xaa Pro Ile Asp Asp Thr Glu Ser Gln Thr Thr Ser Val Asn Leu Met Ala Asp Asp Thr Glu Ser Xaa Phe Ala Thr Xaa Thr Xaa Xaa Xaa Xaa Xaa Leu Asp Val Val Xaa Leu Pro Gly Ala Xaa Xaa (SEQ ID NO:39) wherein Xaa at position 1 is Gln or Ser, Xaa at position 23 is Ala or Arg, Xaa at position 27 is Gln or Asn, Xaa at position 29 is any codable amino acid and is preferably selected from the group consisting of Thr, Leu, Ala, Val, Asp, Pro, His, Asn, Ser and Gly, Xaa at positions 30–33 are any codable amino acid and preferably are selected from the group consisting of Thr, Leu, Ala, Val, Asp, Pro, His, Asn, Ser and Gly, or are absent, Xaa at position 38 is Asn or Gly; and the C-terminal Xaa Xaa is an optional dibasic processing site.

More preferably, LS is a DNA sequence encoding a synthetic leader peptide of SEQ ID NO:40:

Gln Pro Ile Asp Asp Xaa Glu Xaa Gln Xaa Xaa Xaa Val Asn Leu Met Ala Asp Asp Xaa Glu Xaa Ala Phe Ala Xaa Gln Xaa Pro Leu Ala Leu Asp Val Val Asn Leu Ile Xaa Met Ala Xaa Xaa (SEQ ID NO:40)
wherein Xaa at positions 6, 8, 10, 11, 12, 20, 22, 26 and 28 are independently any codable amino acid, but preferably, are alanine (A), serine (S), or aspartic acid (D); and the C-terminal Xaa Xaa is an optional dibasic processing site, or LS is a DNA sequence encoding a synthetic leader peptide with the general formula III (SEQ ID NO:41):

Gln Pro Ile Asp Asp Xaa Glu Xaa Gln Xaa Xaa Xaa Val Asn Leu Met Ala Asp Asp Xaa Glu Xaa Ala Phe Ala Xaa Gln Xaa Pro Leu Ala Leu Asp Val Val Asn Leu Ile Xaa Met Ala (SEQ ID NO:41)

wherein Xaa at positions 6, 8, 10, 11, 12, 20, 22, 26 and 28 are independently any codable amino acid, but preferably, are alanine (A), serine (S), or aspartic acid (D). In formulas I and II above, the C-terminal amino acids Xaa Xaa define a yeast processing site which is optional.

In the present context, the expression "leader peptide" is understood to indicate a pro-peptide sequence whose function is to allow the expressed polypeptide product of *gene* optionally fused at its N-terminal to a spacer peptide and/or a sequence of one or more amino acids defining a processing site, to be directed from the endoplasmic reticulum to the Golgi apparatus and further to a secretory vesicle for secretion into the medium, (i.e. exportation of the expressed polypeptide across the cellular membrane and cell wall, if present, or at least through the cellular membrane into the periplasmic space of a cell having a cell wall). The term "synthetic" used in connection with leader peptides is intended to indicate that the leader peptide is one not found in nature, and, especially, the leader peptide sequences of the present invention do not include the α-factor leader sequence or fragments and constructs thereof such as the sequence Gln Pro Val Ile Ser Thr Thr Val Gly Ser Ala Ala Glu Gly Ser Leu Asp Lys Arg (SEQ ID NO:42), and a leader sequence derived from *S. cerevisiae* HSP150 protein having extensive O-linked glycosylation, cf. Simonen, M., Vihinen, H., Jamsa, E., Arumae, U., Kalkkinen, N., and Makarow, M. (1996) The hsp150D-carrier confers secretion competence to the rat nerve growth factor receptor ectodomain in *Saccharomyces cerevisiae*. Yeast 12, 457–466. Jamsa E; Holkeri H; Vihinen H; Wikstrom M; Simonen M; Walse B; Kalkkinen N; Paakkola J; and Makarow M (1995) Structural features of a polypeptide carrier promoting secretion of a beta-lactamase fusion protein in yeast. YEAST 11,1381–91.

The term "signal peptide" is understood to mean a presequence which is predominantly hydrophobic in nature and present as an N-terminal sequence of the precursor form of an extracellular protein, preferably when expressed in yeast. The function of the signal peptide is to allow the expressed protein to be secreted to enter the endoplasmic reticulum. The signal peptide is normally cleaved off in the course of this process. The signal peptide may be heterologous or homologous to the organism producing the protein.

The expression "polypeptide" is intended to indicate a heterologous polypeptide, i.e. a polypeptide or protein which is not produced by the host organism, preferably yeast, in nature as well as a homologous polypeptide, i.e. a polypeptide which is produced by the host organism, preferably a yeast, in nature and any preform thereof. In a preferred embodiment, the DNA construct of the present invention encodes a heterologous polypeptide.

The expression "a codable amino acid" is intended to indicate an amino acid which can be coded for by a triplet ("codon") of nucleotides.

When, in the amino acid sequences given in the present specification, the one or three letter codes of two amino acids, separated by a slash, are given in brackets, e.g. (D/E), this is intended to indicate that the sequence has either the one or the other of these amino acids in the pertinent position.

The expression "heterologous protein" is intended to indicate a protein or polypeptide which is not produced by the host organism in nature, preferably the protein or polypeptide is heterologous in yeast.

The expression "spacer peptide" is intended to indicate an oligopeptide sequence of one or more amino acid residues, preferably 1 to 12 amino acid residues, more preferably about 4 to 6 amino acid residues, such as Glu Glu Ala Glu Pro Lys (SEQ ID NO:43), Glu Glu Gly Glu Pro Lys (SEQ ID NO:44), Glu Glu Ala Glu Ala Glu Ala Glu Pro Lys (SEQ ID NO:45), and Glu Glu Pro Lys (SEQ ID NO:46), which may include a processing site, preferably situated N-terminally and/or C-terminally.

BRIEF DESCRIPTION OF THE DRAWINGS

The present invention is further illustrated with reference to the appended drawings wherein In FIG. 1 the following symbols are used: TPI-PROMOTER: Denotes the TPI gene promoter sequence from *S. cerevisiae.* 2: Denotes the region encoding a signal/leader peptide (e.g. from the YAP3 signal peptide and LA19 leader peptide in conjunction with the Glu Glu Gly Glu Pro Lys (SEQ ID NO:44) N-terminally extended MI3 insulin precursor). TPI-TERMINATOR: Denotes TPI gene terminator sequence of *S. cerevisiae*. TPI-POMBE: Denotes TPI gene from *S. pombe*. Origin: Denotes a sequence from *S. cerevisiae* 2μ plasmid including its origin of DNA replication in *S. cerevisiae*. AMP-R: Sequence from pBR322/pUC13 including the ampicillin resistance gene and an origin of DNA replication in *E. coli*.

FIG. 2 shows an example of a DNA sequence pAK855 (SEQ ID NO:1) encoding the YAP3 signal peptide (SEQ ID NO:36), a leader without potential N-linked glycosylation sites, the TA57 leader, and Glu Glu Gly Glu Pro Lys (SEQ ID NO:44)-MI3 insulin precursor complex.

FIG. 3 shows an example of a DNA sequence (SEQ ID NO:2) encoding the YAP3 signal peptide (SEQ ID NO:37), a leader without potential N-linked glycosylation sites, the leader TA67, and MI3 insulin precursor without N-terminally extension complex.

DETAILED DISCLOSURE OF THE INVENTION

Figure 1:
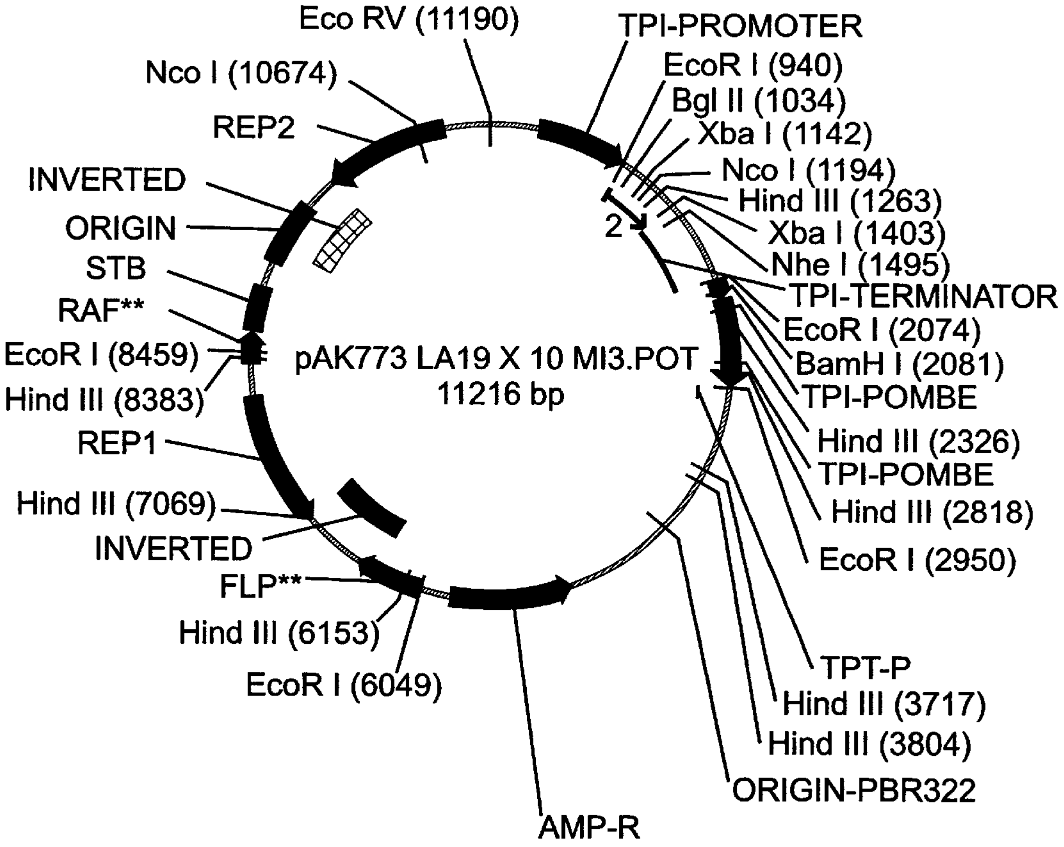
FIG. 1 shows the expression plasmid pAK773 containing genes expressing the N-terminally extended polypeptides of the invention.

Preferred leader sequences of the invention are shown in Table 1 below.

TABLE 1

| Strain | Leader No. | Leader Sequence | SEQ ID NO: |
|---|---|---|---|
| yAK744 | LA23 | Gln Pro Ile Asp Asp Thr Glu Ser Gln Thr Thr Ser Val Asn Leu Met Ala Asp Asp Thr Glu Ser Arg Phe Ala Thr Gln Thr Thr Leu Ala Leu Asp Val Val Asn Leu Ile Ser Met Ala Lys Arg | 3 |
| yAK857 | TA54 | Gln Pro Ile Asp Asp Thr Glu Ser Gln Thr Thr Ser Val Asn Leu Met Ala Asp Asp Thr Glu Ser Arg Phe Ala Thr Gln Thr Pro Leu Ala Leu Asp Val Val Asn Leu Ile Ser Met Ala Lys Arg | 4 |
| yAK858 | TA56 | Gln Pro Ile Asp Asp Thr Glu Ser Gln Thr Thr Ser Val Asn Leu Met Ala Asp Asp Thr Glu Ser Arg Phe Ala Thr Asn Thr Asn Ala Leu Asp Val Val Asn Leu Ile Ser Met Ala Lys Arg | 5 |
| yAK862 | TA57 | Gln Pro Ile Asp Asp Thr Glu Ser Gln Thr Thr Ser Val Asn Leu Met Ala Asp Asp Thr Glu Ser Ala Phe Ala Thr Gln Thr Asn Ser Gly Gly Leu Asp Val Val Gly Leu Ile Ser Met Ala Lys Arg | 6 |
| yAK861 | TA59 | Gln Pro Ile Asp Asp Thr Glu Ser Gln Thr Thr Ser Val Asn Leu Met Ala Asp Asp Thr Glu Ser Ala Phe Ala Thr Gln Thr Thr Ser Val Gly Gly Leu Asp Val Val Gly Leu Ile Ser Met Ala Lys Arg | 7 |

TABLE 1-continued

| Strain | Leader No. | Leader Sequence | SEQ ID NO: |
|---|---|---|---|
| | LA64 | Gln Pro Ile Asp Asp Thr Glu Ser Gln Thr Thr Ser Val Asn Leu Met Ala Asp Asp Thr Glu Ser Arg Phe Ala Thr Gln Thr Thr Leu Ala Leu Asp Val Val Asn Leu Pro Gly Ala Lys Arg | 8 |
| | TA65 | Gln Pro Ile Asp Asp Thr Glu Ser Gln Thr Thr Ser Val Asn Leu Met Ala Asp Asp Thr Glu Ser Ala Phe Ala Thr Gln Thr Asn Ser Gly Gly Leu Asp Val Val Gly Leu Pro Gly Ala Lys Arg | 9 |
| | TA101 | Gln Pro Ile Asp Asp Thr Glu Ser Gln Thr Thr Ser Val Asn Leu Met Ala Asp Asp Thr Glu Ser Ala Phe Ala Thr Gln Thr Asn Ser Gly Gly Leu Asp Val Val Gly Leu Ile Ser Met Ala | 10 |
| | TA67 | Gln Pro Ile Asp Asp Thr Glu Ser Gln Thr Thr Ser Val Asn Leu Met Ala Asp Asp Thr Glu Ser Ala Phe Ala Thr Gln Thr Thr Ser Val Gly Gly Leu Asp Val Val Gly Leu Pro Gly Ala Lys Arg | 11 |
| | TA68 | Gln Pro Ile Asp Asp Thr Glu Ser Gln Thr Thr Ser Val Asn Leu Met Ala Asp Asp Thr Glu Ser Ala Phe Ala Thr Gln Thr Pro Leu Ala Leu Asp Val Val Asn Leu Ile Ser Met Ala Lys Arg | 12 |
| | LA34 | Gln Pro Ile Asp Asp Thr Glu Ser Gln Thr Thr Ser Val Asn Leu Met Ala Asp Asp Thr Glu Ser Arg Phe Ala Thr Gln Thr Thr Leu Ala Leu Asp Val Val Asn Leu Ile Ser Met Ala | 13 |
| | TA76 | Gln Pro Ile Asp Asp Thr Glu Ser Gln Thr Thr Ser Val Asn Leu Met Ala Asp Asp Thr Glu Ser Arg Phe Ala Thr Gln Thr Thr Leu Pro Gly Ala Lys Arg | 14 |
| | TA77 | Gln Pro Ile Asp Asp Thr Glu Ser Gln Thr Thr Ser Val Asn Leu Met Ala Asp Asp Thr Glu Ser Arg Ala Leu Asp Val Val Asn Leu Pro Gly Ala Lys Arg | 15 |
| | TA78 | Gln Pro Ile Asp Asp Thr Glu Ser Gln Thr Thr Ser Val Asn Leu Met Phe Ala Thr Gln Thr Thr Leu Ala Leu Asp Val Val Asn Leu Pro Gly Ala Lys Arg | 16 |
| | TA79 | Gln Pro Ile Asp Asp Thr Glu Ser Gln Ala Asp Asp Thr Glu Ser Arg Phe Ala Thr Gln Thr Thr Leu Ala Leu Asp Val Val Asn Leu Pro Gly Ala Lys Arg | 17 |
| | TA80 | Gln Pro Thr Thr Ser Val Asn Leu Met Ala Asp Asp Thr Glu Ser Arg Phe Ala Thr Gln Thr Thr Leu Ala Leu Asp Val Val Asn Leu Pro Gly Ala Lys Arg | 18 |
| | TA89 | Gln Pro Ile Asp Asp Thr Glu Ser Gln Thr Thr Ser Val Asn Leu Met Ala Asp Asp Thr Glu Ser Ala Phe Ala Thr Gln Thr Asn Ser Gly Gly Leu Asp Val Val Gly Asn Thr Thr Leu Ile Ser Met Ala Lys Arg | 19 |
| | TA90 | Gln Pro Ile Asp Asp Thr Glu Ser Gln Thr Thr Ser Val Asn Leu Met Ala Asp Asp Thr Glu Ser Ala Phe Ala Thr Gln Thr Asn Ser Gly Gly Leu Asp Val Val Gly Leu Ile Asn Thr Thr Met Ala Lys Arg | 20 |

In the sequences of Table 1 the C-terminal KR defines a dibasic protease processing site.

Further preferred leader sequences of the invention are shown in Tables 2 and 3 below.

TABLE 2

| Leader No. | Leader Sequence | SEQ ID NO: |
|---|---|---|
| TA75 | Gln Pro Ile Asp Asp Xaa Glu Xaa Gln Xaa Xaa Xaa Val Asn Leu Met Ala Asp Asp Xaa Glu Xaa Ala Phe Ala Xaa Gln Xaa Pro Leu Ala Leu Asp Val Val Asn Leu Ile Ser Met Ala | 21 |
| TA75.50 | Gln Pro Ile Asp Asp Ala Glu Ala Gln Ala Ala Ala Val Asn Leu Met Ala Asp Asp Asp Glu Gly Phe Ala Ala Gln Ala Pro Leu Ala Leu Asp Val Val Asn Leu Ile Ser Met Ala | 22 |
| TA75.15 | Gln Pro Ile Asp Asp Ala Glu Ala Gln Asp Asp Asp Val Asn Leu Met Ala Asp Asp Asp Gly Arg Phe Ala Asp Gln Ala Pro Leu Ala Leu Asp Val Val Asn Leu Ile Ser Met Ala | 23 |
| TA75.4 | Gln Pro Ile Asp Asp Ala Glu Ala Gln Asp Ala Ala Val Asn Leu Met Ala Asp Asp Gly Arg Leu Lys Ile Arg Phe Ala Ala Gln Ala Pro Leu Ala Leu Asp Val Val Asn Leu Ile Ser Met Ala | 24 |
| TA75.51 | Gln Pro Ile Asp Asp Ala Glu Asp Gln Ala Ala Ala Val Asn Leu Met Ala Asp Asp Asp Glu Asp Gly Phe Ala Ala Gln Ala Pro Leu Ala Leu Asp Val Val Asn Leu Ile Ser Met Ala | 25 |
| TA75.58 | Gln Pro Ile Asp Asp Ala Glu Ala Gln Asp Asp Asp Val Asn Leu Met Ala Asp Asp Asp Gly Arg Phe Ala Ala Gln Ala Pro Leu Ala Leu Asp Val Val Asn Leu Ile Ser Met Ala | 26 |
| TA75.64 | Gln Pro Ile Asp Asp Ala Glu Ala Gln Asp Asp Asp Val Asn Leu Met Ala Asp Asp Asp Gly Arg Phe Ala Ala Gln Ala Pro Leu Ala Leu Asp Val Val Asn Leu Ile Ser Met Ala | 27 |
| | and any of the above where SMA is replaced by $X^1$MA, wherein $X^1$ may be any codable amino acid, preferably hydrophilic amino acids | |

TABLE 3

| Leader No. | Leader Sequence | SEQ ID NO: |
|---|---|---|
| TA91 | Gln Pro Thr Thr Ser Val Asn Leu Met Ala Asp Asp Thr Glu Ser Ala Phe Ala Thr Gln Thr Asn Ser Gly Gly Leu Asp Val Val Gly Leu Ile Ser Met Ala Lys Arg | 28 |
| TA92 | Gln Pro Ile Asp Asp Thr Glu Ser Gln Ala Asp Asp Thr Glu Ser Ala Phe Ala Thr Gln Thr Asn Ser Gly Gly Leu Asp Val Val Gly Leu Ile Ser Met Ala Lys Arg | 29 |
| TA93 | Gln Pro Ile Asp Asp Thr Glu Ser Gln Thr Thr Ser Val Asn Leu Met Phe Ala Thr Gln Thr Asn Ser Gly Gly Leu Asp Val Val Gly Leu Ile Ser Met Ala Lys Arg | 30 |
| TA94 | Gln Pro Ile Asp Asp Thr Glu Ser Gln Thr Thr Ser Val Asn Leu Met Ala Asp Asp Thr Glu Ser Ala Gly Gly Leu Asp Val Val Gly Leu Ile Ser Met Ala Lys Arg | 31 |
| TA95 | Gln Pro Ile Asp Asp Thr Glu Ser Gln Thr Thr Ser Val Asn Leu Met Ala Asp Asp Thr Glu Ser Ala Phe Ala Thr Gln Thr Asn Ser Leu Ile Ser Met Ala Lys Arg | 32 |
| TA96 | Gln Pro Ile Asp Asp Thr Glu Ser Gln Thr Thr Ser Val Asn Leu Met Ala Asp Asp Thr Glu Ser Ala Phe Ala Thr Gln Thr Asn Ser Gly Gly Leu Met Ala Lys Arg | 33 |
| TA97 | Gln Pro Ile Asp Asp Thr Glu Ser Gln Thr Thr Ser Val Asn Leu Met Ala Asp Asp Thr Glu Ser Ala Leu Ile Ser Met Ala Lys Arg | 34 |
| TA98 | Gln Pro Ile Asp Asp Thr Glu Ser Gln Thr Thr Ser Val Asn Leu Met Leu Ile Ser Met Ala Lys Arg | 35 |

The heterologous protein or polypeptide produced by the method of the invention may be any protein which may advantageously be produced in yeast. Preferred examples of such proteins are aprotinin, tissue factor pathway inhibitor or other protease inhibitors, and insulin or insulin precursors, insulin analogues, insulin-like growth factors, such as IGF I and IGF II, human or bovine growth hormone, interleukin, tissue plasminogen activator, glucagon, glucagon-like peptide-1 (GLP 1), glucagon-like peptide-2 (GLP 2), GRPP, Factor VII, Factor VIII, Factor XIII, platelet-derived growth factor, enzymes, such as lipases, or a functional analogue of any one of these proteins. More preferred proteins are precursors of insulin and insulin-like growth factors, and especially the smaller peptides of the proglucagon family, such as glucagon, GLP 1, GLP 2, and GRPP, including truncated forms, such as GLP-1(1-45), GLP-1(1-39), GLP-1(1-38), GLP-1(1-37), GLP-1(1-36), GLP-1(1-35), GLP-1(1-34), GLP-1(7-45), GLP-1(7-39), GLP-1(7-38), GLP-1(7-37), GLP-1(7-36), GLP-1(7-35), and GLP-1(7-34).

In the present context, the term "functional analogue" is meant to indicate a polypeptide with a similar function as the native protein (this is intended to be understood as relating to the nature rather than the level of biological activity of the native protein). The polypeptide may be structurally similar to the native protein and may be derived from the native protein by addition of one or more amino acids to either or both the C- and N-terminal end of the native protein, substitution of one or more amino acids at one or a number of different sites in the native amino acid sequence, deletion of one or more amino acids at either or both ends of the native protein or at one or several sites in the amino acid sequence, or insertion of one or more amino acids at one or more sites in the native amino acid sequence. Such modifications are well known for several of the proteins mentioned above.

The precursors of insulin, including proinsulin as well as precursors having a truncated and/or modified C-peptide or completely lacking a C-peptide, precursors of insulin analogues, and insulin related peptides, such as insulin-like growth factors, may be of human origin or from other animals and recombinant or semisynthetic sources. The cDNA used for expression of the precursors of insulin, precursors of insulin analogues, or insulin related peptides in the method of the invention include codon optimised forms for expression in yeast.

By "a precursor of insulin" or "a precursor an insulin analogue" is to be understood a single-chain polypeptide which by one or more subsequent chemical and/or enzymatical processes can be converted to a two-chain insulin or insulin analogue molecule having the correct establishment of the three disulphide bridges as found in natural human insulin. Preferred insulin precursors are MI1, B(1-29)-A(1-21); MI3, B(1-29)-Ala-Ala-Lys-A(1-21) (as described in e.g. EP 163 529); X14, B(1-27-Asp-Lys)-Ala-Ala-Lys-A(1-21) (SEQ ID NO:47) (as described in e.g. PCT publication No. 95/00550); B(1-27-Asp-Lys)-A(1-21); B(1-27-Asp-Lys)-Ser-Asp-Asp-Ala-Lys-A(1-21) (SEQ ID NO:48); B(1-29)-Ala-Ala-Arg-A(1-21) (as described in e.g. PCT Publication No. 95/07931); MI5, B(1-29)-Ser-Asp-Asp-Ala-Lys-A(1-21) SEQ ID NO:49); and B(1-29)-Ser-Asp-Asp-Ala-Arg-A(1-21), and more preferably MI1, B(1-29)-A(1-21), MI3, B(1-29)-Ala-Ala-Lys-A(1-21) and MI5, B(1-29)-Ser-Asp-Asp-Ala-Lys-A(1-21) (SEQ ID NO:48).

Examples of insulins or insulin analogues which can be produced in this way are human insulin, preferably des(B30) human insulin, porcine insulin; and insulin analogues wherein at least one Lys or Arg is present, preferably insulin analogues wherein $Phe^{B1}$ has been deleted, insulin analogues wherein the A-chain and/or the B-chain have an N-terminal extension and insulin analogues wherein the A-chain and/or the B-chain have a C-terminal extension. Other preferred insulin analogues are such wherein one or more of the amino acid residues, preferably one, two, or three of them, have been substituted by another codable amino acid residue. Thus, in position A21 a parent insulin may instead of Asn have an amino acid residue selected from the group comprising Ala, Gln, Glu, Gly, His, Ile, Leu, Met, Ser, Thr, Trp, Tyr or Val, in particular an amino acid residue selected from the group comprising Gly, Ala, Ser, and Thr. The insulin analogues may also be modified by a combination of the changes outlined above. Likewise, in position B28 a parent insulin may instead of Pro have an amino acid residue selected from the group comprising Asp and Lys, preferably Asp, and in position B29 a parent insulin may instead of Lys have the amino acid Pro. The expression "a codable amino acid residue" as used herein designates an amino acid residue which can be coded for by the genetic code, i.e. a triplet ("codon") of nucleotides.

The signal sequence (SP) may encode any signal peptide which ensures an effective direction of the expressed polypeptide into the secretory pathway of the cell. The signal peptide may be a naturally occurring signal peptide or functional parts thereof or it may be a synthetic peptide. Suitable signal peptides have been found to be the α-factor signal peptide, the signal peptide of mouse salivary amylase, a modified carboxypeptidase signal peptide, the yeast BAR1 signal peptide or the *Humicola lanuginosa* lipase signal peptide or a derivative thereof. The mouse salivary amylase signal sequence is described by Hagenbüchle, O. et al., *Nature* 289 (1981) 643–646. The carboxypeptidase signal sequence is described by Valls, L. A. et al., *Cell* 48 (1987) 887–897. The BAR1 signal peptide is disclosed in WO 87/02670. The yeast aspartic protease 3 signal peptide is described in Danish patent application No. 0828/93.

The yeast processing site encoded by the DNA sequence PS may suitably be any paired combination of Lys and Arg, such as LysArg, ArgLys, ArgArg or LysLys which permits processing of the polypeptide by the KEX2 protease of *Saccharomyces cerevisiae* or the equivalent protease in other yeast species (Julius, D. A. et al., *Cell* 37 (1984) 1075). If KEX2 processing is not convenient, e.g. if it would lead to cleavage of the polypeptide product, e.g. due to the presence of two consecutive basic amino acids internally in the desired product, a processing site for another protease may be selected comprising an amino acid combination which is not found in the polypeptide product, e.g. the processing site for $FX_a$, IleGluGlyArg (SEQ ID NO:50) (cf. Sambrook, J., Fritsch, E. F. and Maniatis, T., *Molecular Cloning: A Laboratory Manual*, Cold Spring Harbor Laboratory Press, New York, 1989).

Two of the preferred DNA constructs encoding leader sequences are incorporated in SEQ ID NOS:1 and 2 as shown in FIG. 2 codon 1078–1209, and FIG. 3 codon 1028–1206, or suitable modifications thereof. Examples of suitable modifications of the DNA sequence are nucleotide substitutions which do not give rise to another amino acid sequence of the protein, but which may correspond to the codon usage of the organism, preferably a fungal organism, such as a yeast, into which the DNA construct is inserted or nucleotide substitutions which do give rise to a different amino acid sequence and therefore, possibly, a different protein structure. Other examples of possible modifications are insertion of one or more codons into the sequence, addition of one or more codons at either end of the sequence and deletion of one or more codons at either end of or within the sequence.

One aspect of the invention is a recombinant expression vector carrying any one of the expression casettes 5'-P-SP-LP-(PS)-(S)-(PS)-*gene*-$(T)_i$-3'

5'-P-SP-LP-PS-*gene*-($T_i$-3

5'-P-SP-LP-S-PS-*gene*-$(T)_i$-3'

5'-P-SP-LP-PS-S-*gene*-$(T)_i$-3'

5'-P-SP-LP-S-*gene*-$(T)_i$-3'

5'-P-SP-LP-*gene*-$(T)_i$-3'

5'-P-SP-LP-PS-S-PS-*gene*-$(T)_i$-3' wherein P is a promoter sequence, SP, LP, PS, S, and *gene*, are as defined above, T is a suitable terminator, e.g. the TPI terminator (cf. Alber, T. and Kawasaki, G., *J. Mol. Appl. Genet.* 1 (1982) 419–434), and i is 1 or 0. The vector may be any vector which is capable of replicating in yeast organisms. The promoter may be any DNA sequence which shows transcriptional activity in yeast and may be derived from genes encoding proteins either homologous or heterologous to yeast. The promoter is preferably derived from a gene encoding a protein homologous to yeast. Examples of suitable promoters for use in yeast host cells are the *Saccharomyces cerevisiae* MFα1, TPI, ADH, PGK promoters, or the yeast plasmid 2 m replication genes REP 1–3 and origin of replication. The vector may also comprise a selectable marker, e.g. the *Schizosaccharomyces pombe* TPI gene as described by Russell, P. R., *Gene* 40 (1985) 125–130.

The expression vector of the invention may be any expression vector that is conveniently subjected to recombinant DNA procedures, and the choice of vector will often depend on the host cell into which the vector is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The methods used to ligate the sequence 5'-P-SP-LS-PS-*gene*-$(T)_i$-3' and to insert it into suitable yeast vectors containing the information necessary for yeast replication, are well known to persons skilled in the art (cf., for instance, Sambrook, J., Fritsch, E. F. and Maniatis, T., op. cit.). It will be understood that the vector may be constructed either by first preparing a DNA construct containing the entire sequence 5'-P-SP-LS-PS-*gene*-$(T)_i$-3' and subsequently inserting this fragment into a suitable expression vector, or by sequentially inserting DNA fragments into a suitable vector containing genetic information for the individual elements (such as the promoter sequence, the signal peptide, the leader sequence, the processing site, the polypeptide, and, if present, the terminator sequence) followed by ligation.

In a further aspect, the present invention relates to a process for producing a polypeptide (or protein) in yeast, the process comprising culturing a yeast cell, which is capable of expressing said polypeptide and which is transformed with a yeast expression vector as described above including a leader peptide sequence of the invention, in a suitable medium to obtain expression and secretion of the said polypeptide, after which the polypeptide is recovered from the medium. The term “culturing” includes fermenting a yeast under laboratory and industrial conditions to produce the polypeptide of interest.

Yeasts are fungi of the class Ascomycetes, subclass Hemiascomycetidae. The yeast organism used in the method of the invention may be any suitable yeast organism which, on cultivation, produces large amounts of the desired polypeptide. Examples of suitable yeast organisms may be strains of the yeast species *Saccharomyces cerevisiae, Saccharomyces kluyveri, Saccharomyces uvarum, Schizosaccharomyces pombe, Kluyveromyces lactis, Hansenula polymorpha, Pichia pastoris, Pichia methanolica, Pichia kluyveri, Yarrowia lipolytica, Candida sp., Candida utilis, Candida cacaoi*, Geotrichum sp., and *Geotrichum fermentans*. It is considered obvious for the skilled person in the art to select any other fungal cell, such as cells of the genus Aspergillus, as the host organism.

The transformation of the yeast cells may for instance be effected by protoplast formation followed by transformation in a manner known per se. The medium used to cultivate the cells may be any conventional medium suitable for growing yeast organisms. The secreted polypeptide, a significant proportion of which will be present in the medium in correctly processed form, may be recovered from the medium by conventional procedures including separating the yeast cells from the medium by centrifugation or filtration, precipitating the proteinaceous components of the supernatant or filtrate by means of a salt, e.g. ammonium sulphate, followed by purification by a variety of chromatographic procedures, e.g. ion exchange chromatography, affinity chromatography or the like.

The invention is further described in the following examples which are not to be construed as limiting the scope of the invention as claimed.

EXAMPLES

Construction of the yeast strain expressing the insulin precursor mediated by leaders lacking N-linked glycosylation.

Synthetic genes coding for the leaders without amino acid sequences potential subjected to attachment of N-linked glycosylation in context with the insulin precursor with or without N-terminal extension of N-terminally extention was constructed using the Polymerase Chain Reaction (PCR). Oligonucleotides for PCR were synthesised using an automatic DNA synthesizer (applied Biosystems model 380A) using phosphoramidite chemistry and commercially available reagents (Beaucage, S. L. and Caruthers, M. H., Tetrahedron letters 22 (1981) 1859–1869). The PCR was performed using the Pwo DNA or EHF Polymerase (Boehringer Mannheim GmbH, Sandhoefer Strasse 116, Mannheim, Germany) according to the manufacture's instructions and the PCR mix was overlayed with 100 ul mineral oil (sigma Chemical CO, St. Louis Mo., USA)

| PCR |
|---|
| 5 $\mu$l oligonucleotide (50 pmol) |
| 5 $\mu$l oligonucleotide (50 pmol) |
| 10 $\mu$l 10X PCR buffer |
| 8 $\mu$l dNTP mix |
| 0.5 $\mu$l Pwo or EHF enzyme |
| 0.5 $\mu$l pAK680 plasmid as template (0.2 ug DNA) |
| 71 $\mu$l dest. water |

A total of 12 cycles were performed, one cycle was 94 C for 45 sec.; 40 C for 1 min; 72 C for 1.5 min. The PCR mixture was then loaded onto an 2.5% agarose gel and electrophoresis was performed using standard techniques (Sambrook J, Fritsch El and Maniatis T, Molecular cloning, Cold Spring Harbour Laboratory press, 1989). The resulting DNA fragment was cut out of the agarose gel and isolated by the GENE CLEAN kit (Bio 101 inc., PO BOX 2284, La Jolla, Calif. 92038, USA) according to the manufacturer's instructions.

Certain leader DNA sequences were constructed by overlap PCR reaction as described by Horton, R. M, Cai, Z., Ho, S. N. and Pease, L. R.: Gene splicing by overlap extension: talior-made genes using the polymerase chain reaction. Biotechniques 8 (1990) 528–535.

The purified PCR DNA fragment was dissolved in Des. water and restriction endonucleases buffer and typically cut with the restriction endonucleases BglII and NcoI according to standard techniques (Sambrook J, Fritsch E F and Maniatis T, Molecular cloning, Cold Spring Harbour Laboratory press, 1989). The NcoI-XbaI DNA fragment on 209 nucleotide basepars was subjected to agarose electrophoresis and purified using The GENE CLEAN Kit as described.

The expression plasmid pAK721 or a similar plasmid of the cPOT type (see FIG. 1) was typically cut with the restriction endonucleases BglII and XbaI and the vector fragment of 10849 nucleotide basepairs isolated using The GENE CLEAN Kit as described.

The typically plasmid pAK773 encoding the N-terminally extended EEGEPK (SEQ ID NO:44)-insulin precursor was cut with the restriction endonucleases NcoI and XbaI and the DNA fragment of 209 nucleotide basepars isolated using The GENE CLEAN Kit as described. The three DNA fragments was ligated together using T4 DNA ligase and standard conditions (Sambrook J, Fritsch E F and Maniatis T, Molecular cloning, Cold spring Harbour laboratory press, 1989). The ligation mix was then transformed into a competent *E. coli* strain (R−, M+) followed by selection with ampicillin resistance. Plasmid from the resulting *E. coli* was isolated using standard techniques (Sambrook J, Fritsch E L and Maniatis T, Molecular cloning, Cold spring Harbour laboratory press, 1989), and checked for insert with appropriate restriction endonucleases i.e. BglII, EcoRI, Nco I and XbaI. The selected plasmid was shown by DNA sequence analysis (SEQUENASE, U.S. Biochemical Corp., USA) to encode the DNA sequence for the leader-MI3 insulin precursor DNA and the DNA encoding the leader to be inserted before the DNA encoding the MI3 insulin precursor DNA.

An example on a DNA sequence pAK855 (SEQ ID NO:1) encoding the YAP3 signal peptide—a leader without potential N-linked glycosylation sites, the TA57 leader, EEGEPK (SEQ ID NO:44)-MI3 insulin precursor complex are shown in FIG. 2.

An example on a DNA sequence (SEQ ID NO:2) encoding the YAP3 signal peptide-synthetic leader without potential N-linked glycosylation sites, the TA69 leader, MI3 insulin precursor without N-terminally extension complex are shown in FIG. 3.

Figure 4:
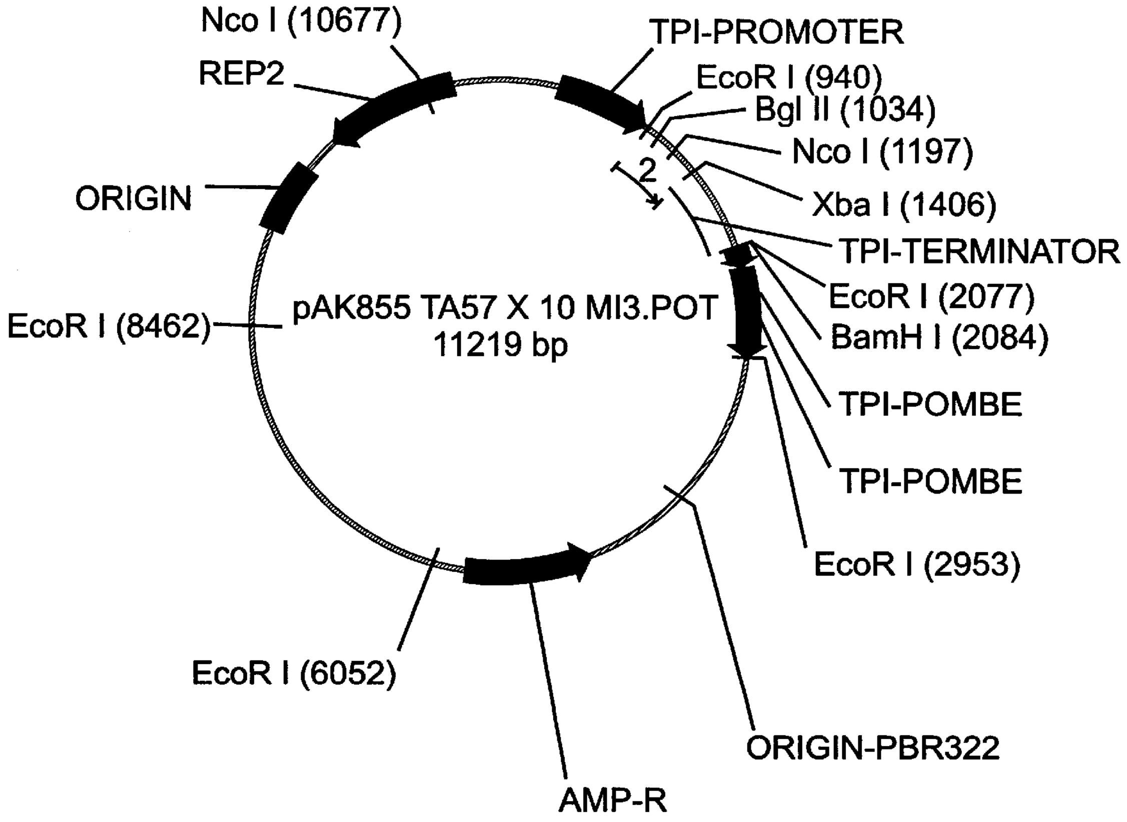
FIG. 4 shows the expression plasmid pAK855 containing genes expressing the leader sequences of the invention.

The yeast expression plasmids used are of the C-POT type (see FIGS. 1 and 4) and are similar to those described in WO EP 171 142, which contain the *Schizosaccharomyces pombe* triose phosphate isomerase gene (POT) for plasmid selection and stabilisation in *S.cerevisiae*. pAK855 also contain the *S. cerevisiae* triose phosphate isomerase promoter and terminator. The promoter and terminator are similar to those described in the plasmid pKFN1003 (described in WO 90/100075) as are all sequences in plasmid except the sequence between the EcoRI-XbaI fragment encoding the YAP3 signal peptide-leader without N-linked glycosylation-MI3 insulin precursor with or without N-terminally extension.

Figure 5:
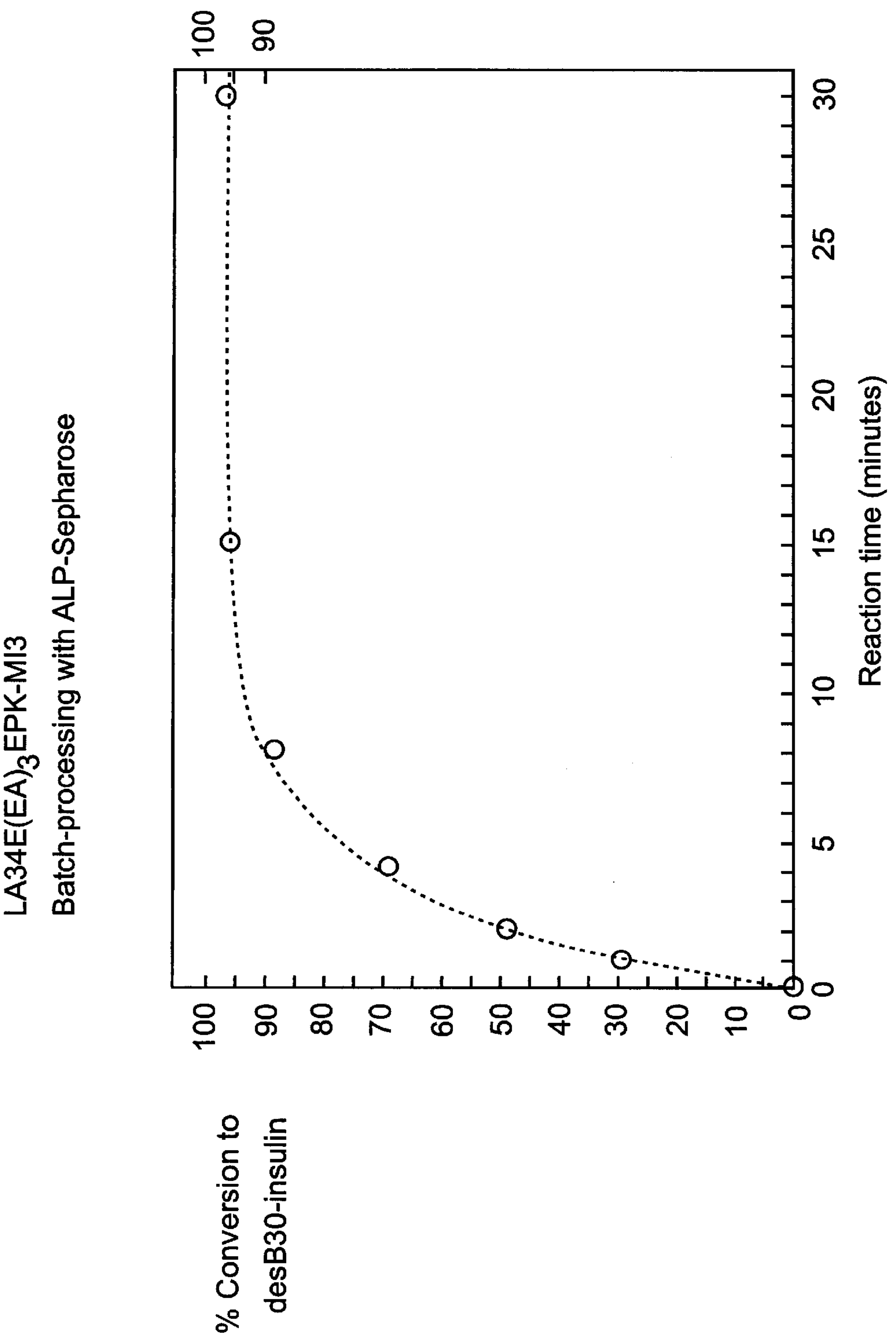
FIG. 5 shows in vitro conversion of LA34/IP fusion protein by Achromobacter lyticus lysyl specific protease as a plot of the conversion of LA34/IP fusion protein by Sepharose-bound Achromobacter lyticus lysyl specific protease vs. time. A curve for a first order reaction with (pseudo-)equilibrium is fitted to the data points.
Figure 6:
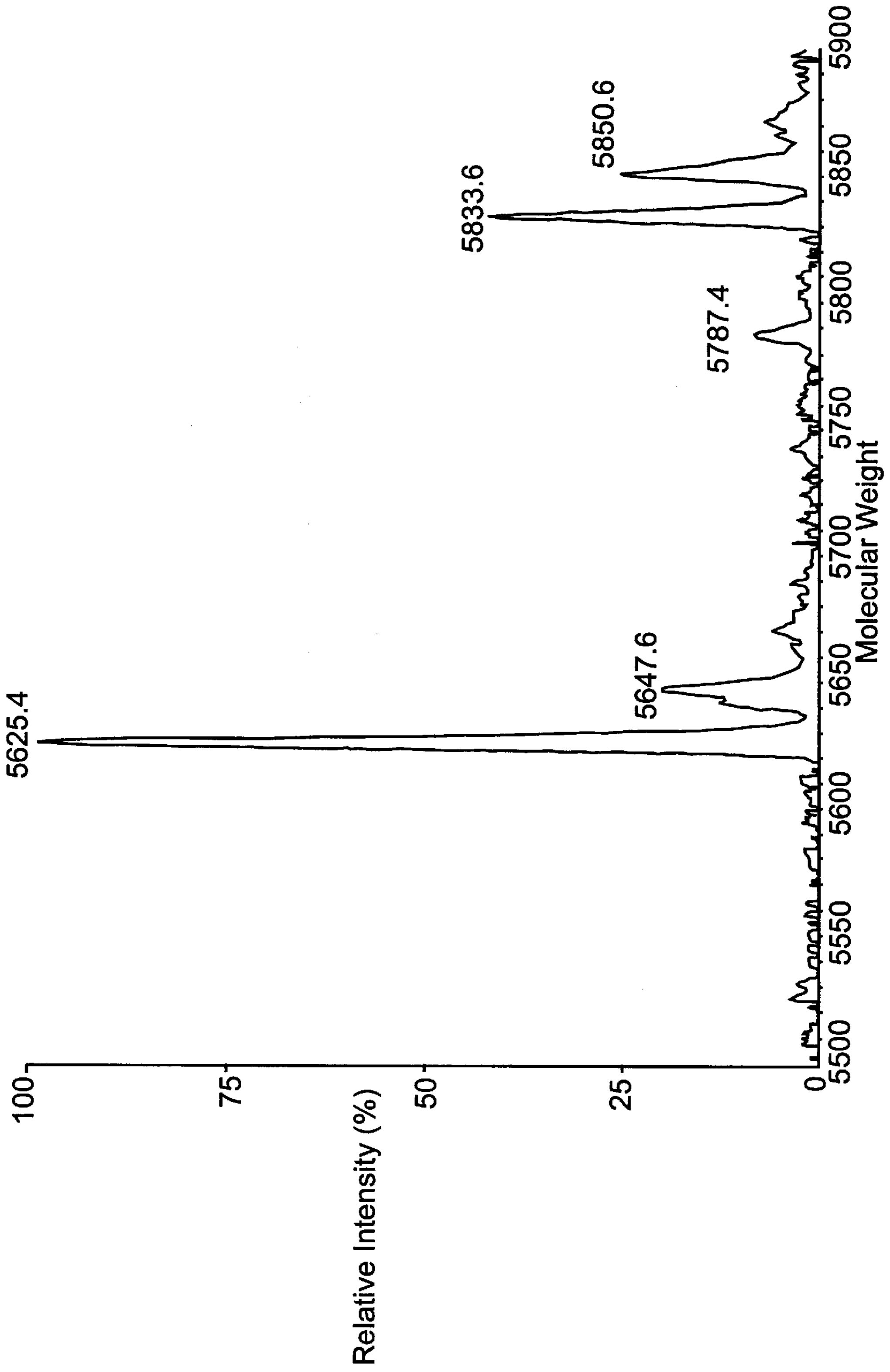
FIG. 6 shows mass spectrometry of in vitro maturation of purified LA34 prepro-leader insulin precursor (MI3) fusion protein by Achromobacter lyticus lysyl specific endoprotease.

Purified LA34/IP fusion protein was processed by SEPHAROSE-bound *Achromobacter lyticus* lysyl specific protease (EC 3.4.21.50) to insulin desB30 (FIG. 5, FIG. 6). From the RP-HPLC analysis results the conversion yield for the removal of the LA34 leader from IP molecule in each collected sample was calculated and then plotted in a graph showing the conversion as a function of the reaction time. A curve for a first-order reaction reaching a (pseudo-) equilibrium can be fitted to the data points as shown in FIG. 5, FIG. 6. Electrospray mass spectrometry was performed on the proteinaceous material isolated from the two main peaks eluted by the RP-HPLC fractionation of the final reaction mixture. For the first eluting peak was found Mw of 5706 Da, corresponding to des(B30)-human insulin (calculated Mw: 5706 Da), and for the second peak was found a Mw of 5625 Da, corresponding to the di-mannosylated LA34-EEAEAEAEPK (SEQ ID NO:45)) polypeptide lacking the dipeptide QP (calculated Mw: 5627 Da) the QP dipeptide presumably having been removed by the dipeptidyl aminopeptidase during secretion. This means that within the reaction time an almost complete cleavage of the precursor to an active desB30 insulin molecule has taken place.

What is claimed is:

1. A DNA construct for use in transforming a yeast cell encoding a heterologous polypeptide and having the structure SP-LP-(PS)-(S)-(PS)-*gene*, wherein SP is a DNA sequence (presequence) encoding a signal peptide, LP is a DNA sequence encoding a synthetic leader peptide (propeptide) wherein N-linked glycosylation is lacking and does not comprise the sequence Gln Pro Val Ile Ser Thr Thr Val Gly Ser Ala Ala Glu Gly Ser Lou Asp Lys Arg (SEQ ID NO:42), PS is a DNA sequence encoding a protease processing site which is optional in both positions, S is a DNA sequence encoding a spacer peptide which is optional, and

*gene* is a DNA sequence encoding a polypeptide.

2. The DNA construct of claim 1, wherein LP is not O-linked glycosylated.

3. A DNA construct of claim 1, wherein LP is O-linked glycosylated.

4. The DNA construct of claim 1, wherein LP does not comprise the consensus N-linked glycosylation sites Asn Xaa Thr/Ser, wherein X is any codable amino acid.

5. The DNA construct of claim 1, wherein SP is a DNA sequence selected from the group consisting of DNA sequences encoding the *S. cerevisiae* α-factor signal peptide, the signal peptide of mouse salivary amylase, the yeast carboxypeptidase signal peptide, the yeast aspartic protease 3 signal peptide and the yeast Bar1 signal peptide.

6. The DNA construct of claim 1, wherein LS is a DNA sequence encoding a synthetic leader sequence of SEQ ID NO:40:

wherein Xaa at positions 6, 8, 10, 11, 12, 20, 22, 26 and 28 are independently any codable amino acid or alanine (Ala), serine (Ser), or aspartic acid (Asp) and the C-terminal Xaa Xaa is an optional dibasic processing site.

7. The DNA construct of claim 1, wherein LS is a DNA sequence encoding a synthetic leader peptide of SEQ ID NO:41 wherein Xaa at positions 6, 8, 10, 11, 12, 20, 22, 26 and 28 are independently any codable amino acid or alanine (Ala), serine (Ser), or aspartic acid (Asp).

8. The DNA construct of claim 1, wherein LP codes for a leader peptide selected from the group consisting of LA23, TA54, TA56, TA57, TA59, LA64, TA65, TA67, TA68, TA76, TA77, TA78, TA79, TA80, TA89, TA90, and TA101 of Table 1 herein.

9. The DNA construct of claim 1, wherein LP codes for a leader peptide selected from the group consisting of TA75, TA75.50, TA75.15, TA75.4, TA75.51, TA75.58, and TA75.64 of Table 2 herein.

10. The DNA construct of claim 1, wherein LP codes for a leader peptide selected from the group consisting of TA91, TA92, TA93, TA94, TA95, TA96, TA97, and TA98, of Table 3 herein.

11. The DNA construct of claim 1, further comprising a promoter sequence located at the 5' end of the DNA sequence encoding the SP-LP-PS-*gene*.

12. An expression cassette comprising the DNA construct of claim 1, a 5' terminally located promoter sequence and a terminator sequence $(T)_i$ located at the 3' terminal of the structure SP-LP-PS-*gene*, where i is 0 or 1.

13. The DNA construct of claim 1 having the structure SP-LP-PS-*gene*.

14. The DNA construct of claim 13, further comprising a sequence encoding a spacer peptide located at the 5' end of *gene* and optionally comprises a sequence encoding a protease processing site located between the 3' end of the sequence encoding said spacer peptide and the 5' end of said *gene*.

15. The DNA construct of claim 1, wherein LP is a DNA sequence encoding a leader peptide of SEQ ID NO:38 or 39 wherein Xaa at position 1 is Gin or Ser, Xaa at position 23 is Ala or Arg, Xaa at position 27 is Gin or Asn, Xaa at position 29 is any codable amino acid or selected from the group consisting of Thr, Leu, Ala, Val, Asp, Pro, His, Asn, Ser and Gly, Xaa at positions 30–33 are any codable amino acid or selected from the group consisting of Thr, Leu, Ala, Val, Asp, Pro, His, Asn, Ser and Gly, or is absent, Xaa at position 38 is Asn or Gly; and the C-terminal Xaa Xaa is a optional dibasic processing site.

16. The DNA construct of claim 15, wherein Xaa at position 27 is Gln and Xaa at positions 29–33 are not Ser or Thr.

17. The DNA construct of claim 16, wherein Xaa at positions 29–33 is selected from the group consisting of Asn Ala, Thr Leu Ala, Asp Leu Ala, Pro Leu Ala, Thr Leu Ala Gly Gly (SEQ ID NO:52), Thr Leu Ala Asp Asp (SEQ ID NO:53), Thr Leu Ala Gly Asp (SEQ ID NO:54), Asn Ser Gly Gly (SEQ ID NO:55), Thr Asn Ser Gly Gly (SEQ ID NO:56), and Thr Ser Val Gly Gly (SEQ ID NO:57).

18. The DNA construct of claim 1, wherein PS is a DNA sequence encoding an endoprotease processing site which allows in vivo processing.

19. A DNA construct of claim 18, wherein the processing site is selected from the group of DNA sequences encoding a dibasic processing site consisting of Lys Arg, Arg Lys, Arg Arg, and Lys Lys.

20. A DNA construct of claim 1, wherein PS is a DNA sequence encoding an endoprotease processing site which allows in vitro processing.

21. A DNA construct of claim 20, wherein the processing site is selected from DNA sequences encoding a monobasic or dibasic processing site comprising the amino acid sequences Lys, Arg, or Lys Arg, Arg Lys, Arg Arg, or Lys Lys.

22. The DNA construct of claim 1, wherein the polypeptide is selected from the group consisting of aprotinin, tissue factor pathway inhibitor, or other protease inhibitors, insulin or insulin precursors, insulin-like polypeptides, insulin-like growth factor I and insulin-like growth factor II, human or bovine growth hormone, interleukin, glucagon, glucagon-like peptide 1, glucagon-like peptide II, GRPP, tissue plasminogen activator, transforming growth factor a or b, platelet-derived growth factor, and enzymes.

23. The DNA construct of claim 22, wherein the polypeptide is selected from the group consisting of insulin or insulin precursors, insulin-like polypeptides, insulin-like growth factor I and insulin-like growth factor II, glucagon, glucagon-like peptide I, glucagon-like peptide II, and GRPP.

24. A DNA construct of claim 1, further comprising a promoter sequence located at the N-terminal end of the structure SP-LP-(PS)-(S)-(PS)-*gene*.

25. The DNA construct of claim 24, wherein the promoter sequence is a yeast promoter sequence.

26. The DNA construct of claim 25, wherein the promoter sequence is the TPI promoter.

27. An expression cassette comprising the DNA construct of claim 1, a 5' terminally located promoter sequence and a terminator sequence $(T)_i$ located at the 3' terminal of the structure SP-LP-(PS)-(S)-(PS)-*gene*, where i is 0 or 1.

28. The expression cassette of claim 27, wherein i is 1 and T is a DNA sequence encoding the TPI terminator.

29. A yeast expression vector comprising the DNA construct of claim 1.

30. A yeast cell which expresses a heterologous polypeptide and which is transformed with the yeast expression vector of claim 29.

31. The yeast cell of claim 30 selected from the group consisting of *Saccharomyces cerevisiae, Saccharomyces uvae, Saccharomyces kluyveri, Schizosaccharomyces pombe, Sacchoromyces uvarum, Kluyveromyces lactis, Hansenula polymorpha, Pichia pastoris, Pichia methanolica, Pichia kluyveri, Yarrowia lipolytica*, Candida sp., *Candida utilis, Candida cacaoi, Geotrichum sp., and Geotrichum fermentans.*

32. A process for producing a heterologous polypeptide in yeast, the process comprising culturing a yeast cell transformed with the yeast expression vector of claim 29, in a suitable medium to obtain expression and secretion of the polypeptide, after which the polypeptide is recovered from the medium.

33. The process of claim 32, wherein the yeast cell is selected from the group consisting of *S. cerevisiae, Saccharomyces uvae, Saccharomyces kluyveri, Schizosaccharomyces pombe, Sacchoromyces uvarum, Kluyveromyces lactis, Hansenula polymorpha, Pichia pastoris, Pichia methanolica, Pichia kluyveri, Yarrowia lipolytica*, Candida sp., *Candida utilis, Candida cacaoi*, Geotrichum sp., and *Geotrichum fermentans*, preferably *Saccharomyces cerevisiae.*

34. A DNA sequence encoding a synthetic prepro-leader peptide lacking the consensus N-linked glycosylation sites Asn Xaa Thr/Ser, wherein X designates any codable amino acid which is not Pro.

* * * * *

UNITED STATES PATENT AND TRADEMARK OFFICE

CERTIFICATE OF CORRECTION

PATENT NO. : 6,214,547 B1
DATED : April 10, 2001
INVENTOR(S) : Kjeldsen et al.

It is certified that error appears in the above-identified patent and that said Letters Patent is hereby corrected as shown below:

Title page,
Item [75] Inventors, delete "Petterson" and insert -- Pettersson --.

Column 39,
Line 27, delete "Lou" and insert -- Leu --.

Column 40,
Lines 38 and 40, delete "Gin" and insert -- Gln --.

Column 41,
Line 22, delete "peptide I" and insert -- peptide 1 --.

Signed and Sealed this

Twenty-first Day of May, 2002

*Attest:*

JAMES E. ROGAN
*Director of the United States Patent and Trademark Office*

*Attesting Officer*

SEQUENCE LISTING

<160> NUMBER OF SEQ ID NOS: 57

<210> SEQ ID NO 1
<211> LENGTH: 550
<212> TYPE: DNA
<213> ORGANISM: S. cerevisiae

<400> SEQUENCE: 1

```
ttcttgctta aatctataac tacaaaaaac acatacagga attccattca agaatagttc     60

aaacaagaag attacaaact atcaatttca tacacaatat aaacgattaa aagaatgaaa    120

ctgaaaactg taagatctgc ggtcctttcg tcactctttg catctcaggt ccttggccaa    180

ccaattgacg acactgaatc tcaaactact tctgtcaact tgatggctga cgacactgaa    240

tctgctttcg ctactcaaac taactctggt ggtttggatg ttgttggttt gatctccatg    300

gctaagagag aagaaggtga accaaagttc gttaaccaac acttgtgcgg ttcccacttg    360

gttgaagctt tgtacttggt ttgcggtgaa agaggtttct tctacactcc taaggctgct    420

aagggtattg tcgaacaatg ctgtacctcc atctgctcct tgtaccaatt ggaaaactac    480

tgcaactaga cgcagcccgc aggctctaga aactaagatt aatataatta tataaaaata    540

ttatcttctt                                                           550
```

<210> SEQ ID NO 2
<211> LENGTH: 500
<212> TYPE: DNA
<213> ORGANISM: S. cerevisiae

<400> SEQUENCE: 2

```
ttcttgctta aatctataac tacaaaaaac acatacagga attccattca agaatagttc     60

aaacaagaag attacaaact atcaatttca tacacaatat aaacgattaa aagaatgaaa    120

ctgaaaactg taagatctgc ggtcctttcg tcactctttg catctcaggt ccttggccaa    180

ccaattgacg acactgaatc tcaaactact tctgtcaact tgatggctga cgacactgaa    240

tctgctttcg ctactcaaac taactctggt ggtttggatg ttgttggttt gccaggtgct    300

aagagattcg ttaaccaaca cttgtgcggt tcccacttgg ttgaagcttt gtacttggtt    360

tgcggtgaaa gaggtttctt ctacactcct aaggctgcta agggtattgt cgaacaatgc    420

tgtacctcca tctgctcctt gtaccaattg gaaaactact gcaactagac gcagcccgca    480

ggctctagaa actaagatta                                                500
```

<210> SEQ ID NO 3
<211> LENGTH: 43
<212> TYPE: PRT
<213> ORGANISM: S. cerevisiae

<400> SEQUENCE: 3

```
Gln Pro Ile Asp Asp Thr Glu Ser Gln Thr Thr Ser Val Asn Leu Met
 1               5                  10                  15

Ala Asp Asp Thr Glu Ser Arg Phe Ala Thr Gln Thr Thr Leu Ala Leu
            20                  25                  30

Asp Val Val Asn Leu Ile Ser Met Ala Lys Arg
        35                  40
```

<210> SEQ ID NO 4
<211> LENGTH: 86
<212> TYPE: PRT

-continued

```
<213> ORGANISM: S. cerevisiae

<400> SEQUENCE: 4

Gln Pro Ile Asp Asp Thr Glu Ser Gln Thr Thr Ser Val Asn Leu Met
 1               5                  10                  15

Ala Asp Asp Thr Glu Ser Arg Phe Ala Thr Gln Thr Pro Leu Ala Leu
            20                  25                  30

Asp Val Val Asn Leu Ile Ser Met Ala Lys Arg Gln Pro Ile Asp Asp
        35                  40                  45

Thr Glu Ser Gln Thr Thr Ser Val Asn Leu Met Ala Asp Asp Thr Glu
    50                  55                  60

Ser Arg Phe Ala Thr Gln Thr Pro Leu Ala Leu Asp Val Val Asn Leu
65                  70                  75                  80

Ile Ser Met Ala Lys Arg
                85


<210> SEQ ID NO 5
<211> LENGTH: 42
<212> TYPE: PRT
<213> ORGANISM: S. cerevisiae

<400> SEQUENCE: 5

 Gln Pro Ile Asp Asp Thr Glu Ser Gln Thr Thr Ser Val Asn Leu Met
  1               5                  10                  15

 Ala Asp Asp Thr Glu Ser Arg Phe Ala Thr Asn Thr Asn Ala Leu Asp
             20                  25                  30

 Val Val Asn Leu Ile Ser Met Ala Lys Arg
         35                  40


<210> SEQ ID NO 6
<211> LENGTH: 44
<212> TYPE: PRT
<213> ORGANISM: S. cerevisiae

<400> SEQUENCE: 6

 Gln Pro Ile Asp Asp Thr Glu Ser Gln Thr Thr Ser Val Asn Leu Met
  1               5                  10                  15

 Ala Asp Asp Thr Glu Ser Ala Phe Ala Thr Gln Thr Asn Ser Gly Gly
             20                  25                  30

 Leu Asp Val Val Gly Leu Ile Ser Met Ala Lys Arg
         35                  40


<210> SEQ ID NO 7
<211> LENGTH: 45
<212> TYPE: PRT
<213> ORGANISM: S. cerevisiae

<400> SEQUENCE: 7

 Gln Pro Ile Asp Asp Thr Glu Ser Gln Thr Thr Ser Val Asn Leu Met
  1               5                  10                  15

 Ala Asp Asp Thr Glu Ser Ala Phe Ala Thr Gln Thr Thr Ser Val Gly
             20                  25                  30

 Gly Leu Asp Val Val Gly Leu Ile Ser Met Ala Lys Arg
         35                  40                  45


<210> SEQ ID NO 8
<211> LENGTH: 42
<212> TYPE: PRT
<213> ORGANISM: S. cerevisiae
```

-continued

<400> SEQUENCE: 8

```
Gln Pro Ile Asp Asp Thr Glu Ser Gln Thr Thr Ser Val Asn Leu Met
 1               5                  10                  15

Ala Asp Asp Thr Glu Ser Arg Phe Ala Thr Gln Thr Thr Leu Ala Leu
            20                  25                  30

Asp Val Val Asn Leu Pro Gly Ala Lys Arg
        35                  40
```

<210> SEQ ID NO 9
<211> LENGTH: 43
<212> TYPE: PRT
<213> ORGANISM: S. cerevisiae

<400> SEQUENCE: 9

```
Gln Pro Ile Asp Asp Thr Glu Ser Gln Thr Thr Ser Val Asn Leu Met
 1               5                  10                  15

Ala Asp Asp Thr Glu Ser Ala Phe Ala Thr Gln Thr Asn Ser Gly Gly
            20                  25                  30

Leu Asp Val Val Gly Leu Pro Gly Ala Lys Arg
        35                  40
```

<210> SEQ ID NO 10
<211> LENGTH: 42
<212> TYPE: PRT
<213> ORGANISM: S. cerevisiae

<400> SEQUENCE: 10

```
Gln Pro Ile Asp Asp Thr Glu Ser Gln Thr Thr Ser Val Asn Leu Met
 1               5                  10                  15

Ala Asp Asp Thr Glu Ser Ala Phe Ala Thr Gln Thr Asn Ser Gly Gly
            20                  25                  30

Leu Asp Val Val Gly Leu Ile Ser Met Ala
        35                  40
```

<210> SEQ ID NO 11
<211> LENGTH: 44
<212> TYPE: PRT
<213> ORGANISM: S. cerevisiae

<400> SEQUENCE: 11

```
Gln Pro Ile Asp Asp Thr Glu Ser Gln Thr Thr Ser Val Asn Leu Met
 1               5                  10                  15

Ala Asp Asp Thr Glu Ser Ala Phe Ala Thr Gln Thr Thr Ser Val Gly
            20                  25                  30

Gly Leu Asp Val Val Gly Leu Pro Gly Ala Lys Arg
        35                  40
```

<210> SEQ ID NO 12
<211> LENGTH: 43
<212> TYPE: PRT
<213> ORGANISM: S. cerevisiae

<400> SEQUENCE: 12

```
Gln Pro Ile Asp Asp Thr Glu Ser Gln Thr Thr Ser Val Asn Leu Met
 1               5                  10                  15

Ala Asp Asp Thr Glu Ser Ala Phe Ala Thr Gln Thr Pro Leu Ala Leu
            20                  25                  30

Asp Val Val Asn Leu Ile Ser Met Ala Lys Arg
        35                  40
```

-continued

```
<210> SEQ ID NO 13
<211> LENGTH: 41
<212> TYPE: PRT
<213> ORGANISM: S. cerevisiae

<400> SEQUENCE: 13

Gln Pro Ile Asp Asp Thr Glu Ser Gln Thr Thr Ser Val Asn Leu Met
1               5                   10                  15

Ala Asp Asp Thr Glu Ser Arg Phe Ala Thr Gln Thr Thr Leu Ala Leu
            20                  25                  30

Asp Val Val Asn Leu Ile Ser Met Ala
        35                  40


<210> SEQ ID NO 14
<211> LENGTH: 35
<212> TYPE: PRT
<213> ORGANISM: S. cerevisiae

<400> SEQUENCE: 14

Gln Pro Ile Asp Asp Thr Glu Ser Gln Thr Thr Ser Val Asn Leu Met
1               5                   10                  15

Ala Asp Asp Thr Glu Ser Arg Phe Ala Thr Gln Thr Thr Leu Pro Gly
            20                  25                  30

Ala Lys Arg
        35


<210> SEQ ID NO 15
<211> LENGTH: 35
<212> TYPE: PRT
<213> ORGANISM: S. cerevisiae

<400> SEQUENCE: 15

Gln Pro Ile Asp Asp Thr Glu Ser Gln Thr Thr Ser Val Asn Leu Met
1               5                   10                  15

Ala Asp Asp Thr Glu Ser Arg Ala Leu Asp Val Val Asn Leu Pro Gly
            20                  25                  30

Ala Lys Arg
        35


<210> SEQ ID NO 16
<211> LENGTH: 35
<212> TYPE: PRT
<213> ORGANISM: S. cerevisiae

<400> SEQUENCE: 16

Gln Pro Ile Asp Asp Thr Glu Ser Gln Thr Thr Ser Val Asn Leu Met
1               5                   10                  15

Phe Ala Thr Gln Thr Thr Leu Ala Leu Asp Val Val Asn Leu Pro Gly
            20                  25                  30

Ala Lys Arg
        35


<210> SEQ ID NO 17
<211> LENGTH: 35
<212> TYPE: PRT
<213> ORGANISM: S. cerevisiae

<400> SEQUENCE: 17

Gln Pro Ile Asp Asp Thr Glu Ser Gln Ala Asp Asp Thr Glu Ser Arg
1               5                   10                  15
```

-continued

```
Phe Ala Thr Gln Thr Thr Leu Ala Leu Asp Val Val Asn Leu Pro Gly
            20                  25                  30

Ala Lys Arg
        35


<210> SEQ ID NO 18
<211> LENGTH: 35
<212> TYPE: PRT
<213> ORGANISM: S. cerevisiae

<400> SEQUENCE: 18

Gln Pro Thr Thr Ser Val Asn Leu Met Ala Asp Asp Thr Glu Ser Arg
 1               5                  10                  15

Phe Ala Thr Gln Thr Thr Leu Ala Leu Asp Val Val Asn Leu Pro Gly
            20                  25                  30

Ala Lys Arg
        35


<210> SEQ ID NO 19
<211> LENGTH: 47
<212> TYPE: PRT
<213> ORGANISM: S. cerevisiae

<400> SEQUENCE: 19

Gln Pro Ile Asp Asp Thr Glu Ser Gln Thr Thr Ser Val Asn Leu Met
 1               5                  10                  15

Ala Asp Asp Thr Glu Ser Ala Phe Ala Thr Gln Thr Asn Ser Gly Gly
            20                  25                  30

Leu Asp Val Val Gly Asn Thr Thr Leu Ile Ser Met Ala Lys Arg
        35                  40                  45


<210> SEQ ID NO 20
<211> LENGTH: 46
<212> TYPE: PRT
<213> ORGANISM: S. cerevisiae

<400> SEQUENCE: 20

Gln Pro Ile Asp Asp Thr Glu Ser Gln Thr Thr Ser Val Asn Leu Met
 1               5                  10                  15

Ala Asp Asp Thr Glu Ser Ala Phe Ala Thr Gln Thr Asn Ser Gly Gly
            20                  25                  30

Leu Asp Val Val Gly Leu Ile Asn Thr Thr Met Ala Lys Arg
        35                  40                  45


<210> SEQ ID NO 21
<211> LENGTH: 41
<212> TYPE: PRT
<213> ORGANISM: S. cerevisiae
<220> FEATURE:
<221> NAME/KEY: PEPTIDE
<222> LOCATION: 1-41
<223> OTHER INFORMATION: Xaa at positions 6, 8, 10-12, 20, 22, 26 and
      28 is alanine/aspartic acid

<400> SEQUENCE: 21

Gln Pro Ile Asp Asp Xaa Glu Xaa Gln Xaa Xaa Xaa Val Asn Leu Met
 1               5                  10                  15

Ala Asp Asp Xaa Glu Xaa Ala Phe Ala Xaa Gln Xaa Pro Leu Ala Leu
            20                  25                  30

Asp Val Val Asn Leu Ile Ser Met Ala
        35                  40
```

-continued

<210> SEQ ID NO 22
<211> LENGTH: 40
<212> TYPE: PRT
<213> ORGANISM: S. cerevisiae

<400> SEQUENCE: 22

Gln Pro Ile Asp Asp Ala Glu Ala Gln Ala Ala Ala Val Asn Leu Met
1 5 10 15

Ala Asp Asp Asp Glu Gly Phe Ala Ala Gln Ala Pro Leu Ala Leu Asp
20 25 30

Val Val Asn Leu Ile Ser Met Ala
35 40

<210> SEQ ID NO 23
<211> LENGTH: 40
<212> TYPE: PRT
<213> ORGANISM: S. cerevisiae

<400> SEQUENCE: 23

Gln Pro Ile Asp Asp Ala Glu Ala Gln Asp Asp Asp Val Asn Leu Met
1 5 10 15

Ala Asp Asp Asp Gly Arg Phe Ala Asp Gln Ala Pro Leu Ala Leu Asp
20 25 30

Val Val Asn Leu Ile Ser Met Ala
35 40

<210> SEQ ID NO 24
<211> LENGTH: 43
<212> TYPE: PRT
<213> ORGANISM: S. cerevisiae

<400> SEQUENCE: 24

Gln Pro Ile Asp Asp Ala Glu Ala Gln Asp Ala Ala Val Asn Leu Met
1 5 10 15

Ala Asp Asp Gly Arg Leu Lys Ile Arg Phe Ala Ala Gln Ala Pro Leu
20 25 30

Ala Leu Asp Val Val Asn Leu Ile Ser Met Ala
35 40

<210> SEQ ID NO 25
<211> LENGTH: 41
<212> TYPE: PRT
<213> ORGANISM: S. cerevisiae

<400> SEQUENCE: 25

Gln Pro Ile Asp Asp Ala Glu Asp Gln Ala Ala Ala Val Asn Leu Met
1 5 10 15

Ala Asp Asp Asp Glu Asp Gly Phe Ala Ala Gln Ala Pro Leu Ala Leu
20 25 30

Asp Val Val Asn Leu Ile Ser Met Ala
35 40

<210> SEQ ID NO 26
<211> LENGTH: 40
<212> TYPE: PRT
<213> ORGANISM: S. cerevisiae

<400> SEQUENCE: 26

Gln Pro Ile Asp Asp Ala Glu Ala Gln Asp Asp Asp Val Asn Leu Met
1 5 10 15

-continued

```
Ala Asp Asp Asp Gly Arg Phe Ala Ala Gln Ala Pro Leu Ala Leu Asp
            20                  25                  30

Val Val Asn Leu Ile Ser Met Ala
        35                  40


<210> SEQ ID NO 27
<211> LENGTH: 40
<212> TYPE: PRT
<213> ORGANISM: S. cerevisiae

<400> SEQUENCE: 27

Gln Pro Ile Asp Asp Ala Glu Ala Gln Asp Asp Asp Val Asn Leu Met
 1               5                  10                  15

Ala Asp Asp Asp Gly Arg Phe Ala Ala Gln Ala Pro Leu Ala Leu Asp
            20                  25                  30

Val Val Asn Leu Ile Ser Met Ala
        35                  40


<210> SEQ ID NO 28
<211> LENGTH: 37
<212> TYPE: PRT
<213> ORGANISM: S. cerevisiae

<400> SEQUENCE: 28

Gln Pro Thr Thr Ser Val Asn Leu Met Ala Asp Asp Thr Glu Ser Ala
 1               5                  10                  15

Phe Ala Thr Gln Thr Asn Ser Gly Gly Leu Asp Val Val Gly Leu Ile
            20                  25                  30

Ser Met Ala Lys Arg
        35


<210> SEQ ID NO 29
<211> LENGTH: 37
<212> TYPE: PRT
<213> ORGANISM: S. cerevisiae

<400> SEQUENCE: 29

Gln Pro Ile Asp Asp Thr Glu Ser Gln Ala Asp Asp Thr Glu Ser Ala
 1               5                  10                  15

Phe Ala Thr Gln Thr Asn Ser Gly Gly Leu Asp Val Val Gly Leu Ile
            20                  25                  30

Ser Met Ala Lys Arg
        35


<210> SEQ ID NO 30
<211> LENGTH: 37
<212> TYPE: PRT
<213> ORGANISM: S. cerevisiae

<400> SEQUENCE: 30

Gln Pro Ile Asp Asp Thr Glu Ser Gln Thr Thr Ser Val Asn Leu Met
 1               5                  10                  15

Phe Ala Thr Gln Thr Asn Ser Gly Gly Leu Asp Val Val Gly Leu Ile
            20                  25                  30

Ser Met Ala Lys Arg
        35


<210> SEQ ID NO 31
<211> LENGTH: 37
<212> TYPE: PRT
<213> ORGANISM: S. cerevisiae
```

-continued

<400> SEQUENCE: 31

```
Gln Pro Ile Asp Asp Thr Glu Ser Gln Thr Thr Ser Val Asn Leu Met
 1               5                  10                  15

Ala Asp Asp Thr Glu Ser Ala Gly Gly Leu Asp Val Val Gly Leu Ile
            20                  25                  30

Ser Met Ala Lys Arg
        35
```

<210> SEQ ID NO 32
<211> LENGTH: 37
<212> TYPE: PRT
<213> ORGANISM: S. cerevisiae

<400> SEQUENCE: 32

```
Gln Pro Ile Asp Asp Thr Glu Ser Gln Thr Thr Ser Val Asn Leu Met
 1               5                  10                  15

Ala Asp Asp Thr Glu Ser Ala Phe Ala Thr Gln Thr Asn Ser Leu Ile
            20                  25                  30

Ser Met Ala Lys Arg
        35
```

<210> SEQ ID NO 33
<211> LENGTH: 37
<212> TYPE: PRT
<213> ORGANISM: S. cerevisiae

<400> SEQUENCE: 33

```
Gln Pro Ile Asp Asp Thr Glu Ser Gln Thr Thr Ser Val Asn Leu Met
 1               5                  10                  15

Ala Asp Asp Thr Glu Ser Ala Phe Ala Thr Gln Thr Asn Ser Gly Gly
            20                  25                  30

Leu Met Ala Lys Arg
        35
```

<210> SEQ ID NO 34
<211> LENGTH: 30
<212> TYPE: PRT
<213> ORGANISM: S. cerevisiae

<400> SEQUENCE: 34

```
Gln Pro Ile Asp Asp Thr Glu Ser Gln Thr Thr Ser Val Asn Leu Met
 1               5                  10                  15

Ala Asp Asp Thr Glu Ser Ala Leu Ile Ser Met Ala Lys Arg
            20                  25                  30
```

<210> SEQ ID NO 35
<211> LENGTH: 23
<212> TYPE: PRT
<213> ORGANISM: S. cerevisiae

<400> SEQUENCE: 35

```
Gln Pro Ile Asp Asp Thr Glu Ser Gln Thr Thr Ser Val Asn Leu Met
 1               5                  10                  15

Leu Ile Ser Met Ala Lys Arg
            20
```

<210> SEQ ID NO 36
<211> LENGTH: 124
<212> TYPE: PRT
<213> ORGANISM: S. cerevisiae -continued

<400> SEQUENCE: 36

Met Lys Leu Lys Thr Val Arg Ser Ala Val Leu Ser Ser Leu Phe Ala
1 5 10 15

Ser Gln Val Leu Gly Gln Pro Ile Asp Asp Thr Glu Ser Gln Thr Thr
20 25 30

Ser Val Asn Leu Met Ala Asp Asp Thr Glu Ser Ala Phe Ala Thr Gln
35 40 45

Thr Asn Ser Gly Gly Leu Asp Val Val Gly Leu Ile Ser Met Ala Lys
50 55 60

Arg Glu Glu Gly Glu Pro Lys Phe Val Asn Gln His Leu Cys Gly Ser
65 70 75 80

His Leu Val Glu Ala Leu Tyr Leu Val Cys Gly Glu Arg Gly Phe Phe
85 90 95

Tyr Thr Pro Lys Ala Ala Lys Gly Ile Val Glu Gln Cys Cys Thr Ser
100 105 110

Ile Cys Ser Leu Tyr Gln Leu Glu Asn Tyr Cys Asn
115 120

<210> SEQ ID NO 37
<211> LENGTH: 117
<212> TYPE: PRT
<213> ORGANISM: S. cerevisiae

<400> SEQUENCE: 37

Met Lys Leu Lys Thr Val Arg Ser Ala Val Leu Ser Ser Leu Phe Ala
1 5 10 15

Ser Gln Val Leu Gly Gln Pro Ile Asp Asp Thr Glu Ser Gln Thr Thr
20 25 30

Ser Val Asn Leu Met Ala Asp Asp Thr Glu Ser Ala Phe Ala Thr Gln
35 40 45

Thr Asn Ser Gly Gly Leu Asp Val Val Gly Leu Pro Gly Ala Lys Arg
50 55 60

Phe Val Asn Gln His Leu Cys Gly Ser His Leu Val Glu Ala Leu Tyr
65 70 75 80

Leu Val Cys Gly Glu Arg Gly Phe Phe Tyr Thr Pro Lys Ala Ala Lys
85 90 95

Gly Ile Val Glu Gln Cys Cys Thr Ser Ile Cys Ser Leu Tyr Gln Leu
100 105 110

Glu Asn Tyr Cys Asn
115

<210> SEQ ID NO 38
<211> LENGTH: 45
<212> TYPE: PRT
<213> ORGANISM: S. cerevisiae
<220> FEATURE:
<221> NAME/KEY: Peptide
<222> LOCATION: 1-45
<223> OTHER INFORMATION: Xaa at positions 1 = Q or S, 23 = A or R,
27 = Q or N, 29-33 = codable amino acid,38 = N or G, and
44-45 is a basic amino acid

<400> SEQUENCE: 38

Xaa Pro Ile Asp Asp Thr Glu Ser Gln Thr Thr Ser Val Asn Leu Met
1 5 10 15

Ala Asp Asp Thr Glu Ser Xaa Phe Ala Thr Xaa Thr Xaa Xaa Xaa Xaa
20 25 30

-continued

Xaa Leu Asp Val Val Xaa Leu Ile Ser Met Ala Xaa Xaa
35 40 45

<210> SEQ ID NO 39
<211> LENGTH: 44
<212> TYPE: PRT
<213> ORGANISM: S. cerevisiae
<220> FEATURE:
<221> NAME/KEY: Peptide
<222> LOCATION: 1-44
<223> OTHER INFORMATION: Xaa at positions 1 = Q or S, 23 = A or R, 27 = Q or N, 29-33 = codable amino acid, 38 = N or G, 43-44 = is a basic amino acid

<400> SEQUENCE: 39

Xaa Pro Ile Asp Asp Thr Glu Ser Gln Thr Thr Ser Val Asn Leu Met
1 5 10 15

Ala Asp Asp Thr Glu Ser Xaa Phe Ala Thr Xaa Thr Xaa Xaa Xaa Xaa
20 25 30

Xaa Leu Asp Val Val Xaa Leu Pro Gly Ala Xaa Xaa
35 40

<210> SEQ ID NO 40
<211> LENGTH: 43
<212> TYPE: PRT
<213> ORGANISM: S. cerevisiae
<220> FEATURE:
<221> NAME/KEY: Peptide
<222> LOCATION: 1-43
<223> OTHER INFORMATION: Xaa at positions 6, 8, 10-12, 20, 22, 26, 28, 39 = any codable amino acid, preferably A, S or D, and 42-43 = is a basic amino acid

<400> SEQUENCE: 40

Gln Pro Ile Asp Asp Xaa Glu Xaa Gln Xaa Xaa Xaa Val Asn Leu Met
1 5 10 15

Ala Asp Asp Xaa Glu Xaa Ala Phe Ala Xaa Gln Xaa Pro Leu Ala Leu
20 25 30

Asp Val Val Asn Leu Ile Xaa Met Ala Xaa Xaa
35 40

<210> SEQ ID NO 41
<211> LENGTH: 41
<212> TYPE: PRT
<213> ORGANISM: S. cerevisiae
<220> FEATURE:
<221> NAME/KEY: Peptide
<222> LOCATION: 1-41
<223> OTHER INFORMATION: Xaa (at all positions) = any codable amino acid, preferably A, S or D

<400> SEQUENCE: 41

Gln Pro Ile Asp Asp Xaa Glu Xaa Gln Xaa Xaa Xaa Val Asn Leu Met
1 5 10 15

Ala Asp Asp Xaa Glu Xaa Ala Phe Ala Xaa Gln Xaa Pro Leu Ala Leu
20 25 30

Asp Val Val Asn Leu Ile Xaa Met Ala
35 40

<210> SEQ ID NO 42
<211> LENGTH: 19
<212> TYPE: PRT
<213> ORGANISM: S. cerevisiae

<400> SEQUENCE: 42

-continued

Gln Pro Val Ile Ser Thr Thr Val Gly Ser Ala Ala Glu Gly Ser Leu
 1 5 10 15

Asp Lys Arg

<210> SEQ ID NO 43
<211> LENGTH: 6
<212> TYPE: PRT
<213> ORGANISM: S. cerevisiae

<400> SEQUENCE: 43

Glu Glu Ala Glu Pro Lys
 1 5

<210> SEQ ID NO 44
<211> LENGTH: 6
<212> TYPE: PRT
<213> ORGANISM: S. cerevisiae

<400> SEQUENCE: 44

Glu Glu Gly Glu Pro Lys
 1 5

<210> SEQ ID NO 45
<211> LENGTH: 10
<212> TYPE: PRT
<213> ORGANISM: S. cerevisiae

<400> SEQUENCE: 45

Glu Glu Ala Glu Ala Glu Ala Glu Pro Lys
 1 5 10

<210> SEQ ID NO 46
<211> LENGTH: 4
<212> TYPE: PRT
<213> ORGANISM: S. cerevisiae

<400> SEQUENCE: 46

Glu Glu Pro Lys
 1

<210> SEQ ID NO 47
<211> LENGTH: 5
<212> TYPE: PRT
<213> ORGANISM: S. Cerevisiae

<400> SEQUENCE: 47

Asp Lys Ala Ala Lys
1 5

<210> SEQ ID NO 48
<211> LENGTH: 7
<212> TYPE: PRT
<213> ORGANISM: S. Cerevisiae

<400> SEQUENCE: 48

Asp Lys Ser Asp Asp Ala Lys
1 5

<210> SEQ ID NO 49
<211> LENGTH: 5
<212> TYPE: PRT
<213> ORGANISM: S. Cerevisiae

<400> SEQUENCE: 49

-continued

Ser Asp Asp Ala Arg
1 5

<210> SEQ ID NO 50
<211> LENGTH: 4
<212> TYPE: PRT
<213> ORGANISM: S. cerevisiae

<400> SEQUENCE: 50 le Glu Gly Arg
1

<210> SEQ ID NO 51
<211> LENGTH: 6
<212> TYPE: PRT
<213> ORGANISM: S. Cerevisiae

<400> SEQUENCE: 51 ys Arg Glu Ala Glu Ala
1 5

<210> SEQ ID NO 52
<211> LENGTH: 5
<212> TYPE: PRT
<213> ORGANISM: S. Cerevisiae

<400> SEQUENCE: 52 hr Leu Ala Gly Gly
1 5

<210> SEQ ID NO 53
<211> LENGTH: 5
<212> TYPE: PRT
<213> ORGANISM: S. Cerevisiae

<400> SEQUENCE: 53 hr Leu Ala Asp Asp
1 5

<210> SEQ ID NO 54
<211> LENGTH: 5
<212> TYPE: PRT
<213> ORGANISM: S. Cerevisiae

<400> SEQUENCE: 54 hr Leu Ala Gly Asp
1 5

<210> SEQ ID NO 55
<211> LENGTH: 4
<212> TYPE: PRT
<213> ORGANISM: S. Cerevisiae

<400> SEQUENCE: 55 sn Ser Gly Gly
1

<210> SEQ ID NO 56
<211> LENGTH: 5
<212> TYPE: PRT
<213> ORGANISM: S. Cerevisiae

<400> SEQUENCE: 56 hr Asn Ser Gly Gly
1 5

-continued

```
<210> SEQ ID NO 57
<211> LENGTH: 5
<212> TYPE: PRT
<213> ORGANISM: S. Cerevisiae

<400> SEQUENCE: 57

hr Ser Val Gly Gly
1               5
```